(12) United States Patent
Heflin

(10) Patent No.: US 10,034,690 B2
(45) Date of Patent: Jul. 31, 2018

(54) SPINE ALIGNMENT SYSTEM

(71) Applicant: John A. Heflin, Salt Lake City, UT (US)

(72) Inventor: John A. Heflin, Salt Lake City, UT (US)

( * ) Notice: Subject to any disclaimer, the term of this patent is extended or adjusted under 35 U.S.C. 154(b) by 0 days.

(21) Appl. No.: 14/964,490

(22) Filed: Dec. 9, 2015

(65) Prior Publication Data

US 2016/0183983 A1   Jun. 30, 2016

Related U.S. Application Data

(60) Provisional application No. 62/180,870, filed on Jun. 17, 2015, provisional application No. 62/089,725, filed on Dec. 9, 2014.

(51) Int. Cl.
*A61B 17/70* (2006.01)
*A61B 17/68* (2006.01)
*A61B 90/00* (2016.01)

(52) U.S. Cl.
CPC ...... *A61B 17/7034* (2013.01); *A61B 17/7037* (2013.01); *A61B 17/7041* (2013.01); *A61B 17/7086* (2013.01); *A61B 2017/681* (2013.01); *A61B 2090/037* (2016.02)

(58) Field of Classification Search
CPC .................................. A61B 17/7083–17/7088
USPC ......................................... 606/86 A, 305, 308
See application file for complete search history.

(56) References Cited

U.S. PATENT DOCUMENTS

| 3,788,318 A | 1/1974 | Kim et al. |
| 3,789,852 A | 2/1974 | Kim et al. |
| 3,892,232 A | 7/1975 | Neufeld |
| 4,083,370 A | 4/1978 | Taylor |
| 4,350,151 A | 9/1982 | Scott |
| 4,409,968 A | 10/1983 | Drummond |

(Continued)

FOREIGN PATENT DOCUMENTS

| AT | 135551 | 4/1996 |
| AT | 166217 | 6/1998 |

(Continued)

OTHER PUBLICATIONS

Office Action from U.S. Appl. No. 10/868,075, dated Oct. 12, 2007.

(Continued)

*Primary Examiner* — Eduardo C Robert
*Assistant Examiner* — Michelle C Eckman
(74) *Attorney, Agent, or Firm* — Clayton Howarth, P.C.

(57) ABSTRACT

A spine alignment system is disclosed. The spine alignment system includes a pedicle screw having a longitudinal axis, the pedicle screw having a screw head. The screw head includes a slot having a longitudinal axis that is substantially perpendicular to the longitudinal axis of the pedicle screw. An extension shaft is secured to the pedicle screw, such that a longitudinal axis of the extension shaft is substantially coaxial with the longitudinal axis of the pedicle screw. The spine alignment system also includes a cap having a slot that forms a substantially cylindrical passage with the slot of the pedicle screw head. The substantially cylindrical passage is configured to receive an alignment rod such that alignment of the spine occurs as the rod is translated along the extension shaft to the pedicle screw.

38 Claims, 20 Drawing Sheets

(56) References Cited

U.S. PATENT DOCUMENTS

| | | |
|---|---|---|
| 4,411,259 A | 10/1983 | Drummond |
| 4,448,191 A | 5/1984 | Rodnyansky et al. |
| 4,449,532 A | 5/1984 | Storz |
| 4,474,046 A | 10/1984 | Cook |
| 4,545,374 A | 10/1985 | Jacobson |
| 4,611,581 A | 9/1986 | Steffee |
| 4,653,481 A | 3/1987 | Howland et al. |
| 4,790,297 A | 12/1988 | Luque |
| 4,817,587 A | 4/1989 | Janese |
| 4,862,891 A | 9/1989 | Smith |
| 4,887,595 A | 12/1989 | Heinig et al. |
| 4,899,729 A | 2/1990 | Gill et al. |
| 4,913,134 A | 4/1990 | Luque |
| 4,957,495 A | 9/1990 | Kluger |
| 4,961,740 A | 10/1990 | Ray et al. |
| 5,010,879 A | 4/1991 | Moriya et al. |
| 5,015,247 A | 5/1991 | Michelson |
| 5,026,373 A | 6/1991 | Ray et al. |
| 5,027,793 A | 7/1991 | Engelhardt et al. |
| 5,125,396 A | 6/1992 | Ray |
| 5,129,899 A | 7/1992 | Small et al. |
| 5,171,279 A | 12/1992 | Mathews |
| 5,183,464 A | 2/1993 | Dubrul et al. |
| 5,195,541 A | 3/1993 | Obenchain |
| 5,242,443 A | 9/1993 | Kambin |
| 5,290,288 A | 3/1994 | Vignaud et al. |
| 5,295,994 A | 3/1994 | Bonutti |
| D346,217 S | 4/1994 | Sparker et al. |
| 5,357,983 A | 10/1994 | Mathews |
| 5,360,431 A | 11/1994 | Puno et al. |
| 5,373,860 A | 12/1994 | Catone |
| 5,395,317 A | 3/1995 | Kambin |
| 5,409,488 A | 4/1995 | Ulrich |
| 5,425,490 A | 6/1995 | Goble et al. |
| 5,425,732 A | 6/1995 | Ulrich |
| 5,439,464 A | 8/1995 | Shapiro |
| 5,464,406 A | 11/1995 | Ritter et al. |
| 5,474,555 A | 12/1995 | Puno et al. |
| 5,480,440 A | 1/1996 | Kambin |
| 5,484,437 A | 1/1996 | Michelson |
| 5,486,176 A | 1/1996 | Hildebrand et al. |
| 5,489,307 A | 2/1996 | Kuslich et al. |
| 5,490,409 A | 2/1996 | Weber |
| 5,496,322 A | 3/1996 | Mathews |
| 5,505,732 A | 4/1996 | Michelson |
| 5,534,001 A * | 7/1996 | Schlapfer ............ A61B 17/7032 606/302 |
| 5,545,228 A | 8/1996 | Kambin |
| 5,569,248 A | 10/1996 | Mathews |
| 5,569,290 A | 10/1996 | McAfee |
| 5,584,887 A | 12/1996 | Kambin |
| 5,591,165 A | 1/1997 | Jackson |
| 5,593,409 A | 1/1997 | Michelson |
| 5,601,590 A | 2/1997 | Bonutti et al. |
| 5,624,442 A | 4/1997 | Mellinger et al. |
| 5,658,286 A | 8/1997 | Sava |
| 5,700,291 A | 12/1997 | Kuslich et al. |
| 5,720,748 A | 2/1998 | Kuslich et al. |
| 5,720,751 A | 2/1998 | Jackson |
| 5,728,097 A | 3/1998 | Mathews |
| 5,741,253 A | 4/1998 | Michelson |
| 5,741,261 A | 4/1998 | Moskovitz et al. |
| 5,746,720 A | 5/1998 | Stouder, Jr. |
| 5,762,629 A | 6/1998 | Kambin |
| 5,772,661 A | 6/1998 | Michelson |
| 5,782,865 A | 7/1998 | Grotz |
| 5,785,710 A | 7/1998 | Michelson |
| 5,792,044 A | 8/1998 | Foley et al. |
| 5,797,909 A | 8/1998 | Michelson |
| 5,814,046 A | 9/1998 | Hopf |
| 5,882,344 A | 3/1999 | Stouder, Jr. |
| 5,885,291 A | 3/1999 | Moskovitz et al. |
| 5,885,292 A | 3/1999 | Moskovitz et al. |
| 5,891,147 A | 4/1999 | Moskovitz et al. |
| 5,899,908 A | 5/1999 | Kuslich et al. |
| 5,902,231 A | 5/1999 | Foley et al. |
| RE36,221 E | 6/1999 | Breard et al. |
| 5,928,139 A | 7/1999 | Koros et al. |
| 5,928,242 A | 7/1999 | Kuslich et al. |
| 5,938,662 A | 8/1999 | Rinner |
| 5,944,658 A | 8/1999 | Koros et al. |
| 5,947,971 A | 9/1999 | Kuslich et al. |
| 5,954,635 A | 9/1999 | Foley et al. |
| 5,957,888 A | 9/1999 | Hinchliffe |
| 5,961,499 A | 10/1999 | Bonutti et al. |
| 5,964,761 A | 10/1999 | Kambin |
| 5,968,078 A | 10/1999 | Grotz |
| 5,976,146 A | 11/1999 | Ogawa et al. |
| 6,007,487 A | 12/1999 | Foley et al. |
| 6,015,409 A | 1/2000 | Jackson |
| 6,033,406 A | 3/2000 | Mathews |
| 6,035,691 A | 3/2000 | Lin et al. |
| 6,080,155 A | 6/2000 | Michelson |
| 6,090,113 A | 7/2000 | Le Couedic et al. |
| 6,096,038 A | 8/2000 | Michelson |
| 6,120,502 A | 9/2000 | Michelson |
| 6,123,705 A | 9/2000 | Michelson |
| 6,123,707 A | 9/2000 | Wagner |
| 6,127,597 A | 10/2000 | Beyar et al. |
| 6,149,650 A | 11/2000 | Michelson |
| 6,152,871 A | 11/2000 | Foley et al. |
| 6,159,179 A | 12/2000 | Simonson |
| 6,162,170 A | 12/2000 | Foley et al. |
| 6,175,758 B1 | 1/2001 | Kambin |
| 6,183,472 B1 | 2/2001 | Lutz |
| 6,187,000 B1 | 2/2001 | Davison et al. |
| 6,197,002 B1 | 3/2001 | Peterson |
| 6,200,322 B1 | 3/2001 | Branch et al. |
| 6,206,822 B1 | 3/2001 | Foley et al. |
| 6,206,826 B1 | 3/2001 | Mathews et al. |
| 6,210,412 B1 | 4/2001 | Michelson |
| 6,217,509 B1 | 4/2001 | Foley et al. |
| 6,226,548 B1 | 5/2001 | Foley et al. |
| 6,235,028 B1 | 5/2001 | Brumfield et al. |
| 6,248,104 B1 * | 6/2001 | Chopin ............... A61B 17/7041 606/267 |
| 6,287,313 B1 | 9/2001 | Sasso |
| 6,332,780 B1 | 12/2001 | Traxel et al. |
| 6,371,957 B1 * | 4/2002 | Amrein ............... A61B 17/7032 606/270 |
| 6,371,968 B1 | 4/2002 | Kogasaka et al. |
| 6,425,859 B1 | 7/2002 | Foley et al. |
| 6,485,518 B1 | 11/2002 | Cornwall et al. |
| 6,506,151 B1 | 1/2003 | Estes et al. |
| 6,520,907 B1 | 2/2003 | Foley et al. |
| 6,524,320 B2 | 2/2003 | DiPoto |
| 6,530,926 B1 | 3/2003 | Davison |
| 6,530,929 B1 | 3/2003 | Justis et al. |
| 6,562,046 B2 | 5/2003 | Sasso |
| 6,575,979 B1 | 6/2003 | Cragg |
| 6,596,008 B1 | 7/2003 | Kambin |
| 6,605,095 B2 | 8/2003 | Grossman |
| 6,607,530 B1 | 8/2003 | Carl et al. |
| 6,610,063 B2 * | 8/2003 | Kumar ............... A61B 17/7032 606/250 |
| 6,723,095 B2 | 4/2004 | Hammerslag |
| 6,740,089 B2 | 5/2004 | Haider |
| 6,749,614 B2 | 6/2004 | Teitelbaum et al. |
| 6,770,074 B2 | 8/2004 | Michelson |
| 6,793,656 B1 | 9/2004 | Mathews |
| 6,800,084 B2 | 10/2004 | Davison et al. |
| 6,811,558 B2 | 11/2004 | Davison et al. |
| 6,821,277 B2 | 11/2004 | Teitelbaum |
| 6,837,891 B2 | 1/2005 | Davison et al. |
| 6,849,064 B2 | 2/2005 | Hamada |
| 6,875,212 B2 | 4/2005 | Shaolian et al. |
| 6,899,713 B2 | 5/2005 | Shaolian et al. |
| 6,923,811 B1 | 8/2005 | Carl et al. |
| 6,929,647 B2 | 8/2005 | Cohen |
| 6,964,667 B2 | 11/2005 | Shaolian et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,083,621 B2 | 8/2006 | Shaolian et al. |

(56) References Cited

U.S. PATENT DOCUMENTS

| | | | |
|---|---|---|---|
| 7,121,755 B2 * | 10/2006 | Schlapfer | A61B 17/7037 403/123 |
| 7,160,300 B2 | 1/2007 | Jackson | |
| 7,188,626 B2 | 3/2007 | Foley et al. | |
| 7,250,052 B2 | 7/2007 | Landry et al. | |
| 7,306,603 B2 | 12/2007 | Boehm, Jr. et al. | |
| 7,404,818 B2 * | 7/2008 | Miller | A61B 17/7034 606/301 |
| 7,507,248 B2 * | 3/2009 | Beaurain | A61B 17/7037 606/261 |
| 7,713,289 B2 * | 5/2010 | Matthys | A61B 17/7041 606/246 |
| 7,758,617 B2 | 7/2010 | Iott et al. | |
| 7,811,288 B2 | 10/2010 | Jones et al. | |
| 7,927,360 B2 | 4/2011 | Pond, Jr. et al. | |
| 7,942,906 B2 * | 5/2011 | Bishop | A61B 17/7037 606/246 |
| 7,955,355 B2 | 6/2011 | Chin | |
| 8,002,798 B2 | 8/2011 | Chin et al. | |
| 8,025,682 B2 * | 9/2011 | Mahoney | A61B 17/1757 606/264 |
| 8,057,518 B2 * | 11/2011 | Frasier | A61B 17/7034 606/264 |
| 8,157,809 B2 | 4/2012 | Butters et al. | |
| 8,162,988 B2 * | 4/2012 | Delecrin | A61B 17/7007 606/266 |
| 8,177,817 B2 | 5/2012 | Fallin | |
| 8,192,440 B2 | 6/2012 | Jones et al. | |
| 8,221,457 B2 * | 7/2012 | Delecrin | A61B 17/7007 606/246 |
| 8,398,684 B2 * | 3/2013 | Kamran | A61B 17/7001 606/246 |
| 8,663,287 B2 * | 3/2014 | Butler | A61B 17/7037 606/264 |
| 8,951,289 B2 * | 2/2015 | Matityahu | A61B 17/7038 606/250 |
| 8,979,851 B2 | 3/2015 | Fallin et al. | |
| 9,011,447 B2 | 4/2015 | Arnett et al. | |
| 9,078,702 B1 * | 7/2015 | Sims | A61B 17/7077 |
| 9,314,274 B2 * | 4/2016 | Amstutz | A61B 17/7038 |
| 9,326,795 B2 * | 5/2016 | Beaurain | A61B 17/701 |
| 9,358,132 B2 | 6/2016 | Chervitz et al. | |
| 9,408,642 B2 * | 8/2016 | Wong | A61B 17/7041 |
| 9,486,256 B1 * | 11/2016 | Lish | A61B 17/7085 |
| 2001/0011170 A1 | 8/2001 | Davison et al. | |
| 2001/0027320 A1 | 10/2001 | Sasso | |
| 2001/0029353 A1 | 10/2001 | Peterson | |
| 2001/0049498 A1 | 12/2001 | Davison et al. | |
| 2001/0049527 A1 | 12/2001 | Cragg | |
| 2001/0053915 A1 | 12/2001 | Grossman | |
| 2002/0016583 A1 | 2/2002 | Cragg | |
| 2002/0045904 A1 | 4/2002 | Fuss et al. | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0107519 A1 | 8/2002 | Dixon et al. | |
| 2002/0116006 A1 | 8/2002 | Cohen | |
| 2002/0161367 A1 | 10/2002 | Ferree | |
| 2002/0161368 A1 | 10/2002 | Foley et al. | |
| 2002/0169450 A1 * | 11/2002 | Lange | A61B 17/7037 606/250 |
| 2002/0173796 A1 | 11/2002 | Cragg | |
| 2002/0198526 A1 | 12/2002 | Shaolian et al. | |
| 2003/0060824 A1 | 3/2003 | Viart et al. | |
| 2003/0073998 A1 | 4/2003 | Pagliuca et al. | |
| 2003/0083688 A1 | 5/2003 | Simonson | |
| 2003/0139648 A1 | 7/2003 | Foley et al. | |
| 2003/0144664 A1 * | 7/2003 | Cavagna | A61B 17/701 606/265 |
| 2003/0195518 A1 | 10/2003 | Cragg | |
| 2003/0199872 A1 | 10/2003 | Markworth et al. | |
| 2003/0199884 A1 | 10/2003 | Davison et al. | |
| 2003/0204189 A1 | 10/2003 | Cragg | |
| 2003/0208202 A1 | 11/2003 | Falahee | |
| 2003/0225408 A1 | 12/2003 | Nichols et al. | |
| 2003/0229353 A1 | 12/2003 | Cragg | |
| 2004/0006341 A1 | 1/2004 | Shaolian et al. | |
| 2004/0006344 A1 | 1/2004 | Nguyen et al. | |
| 2004/0034351 A1 | 2/2004 | Sherman et al. | |
| 2004/0039384 A1 | 2/2004 | Boehm, Jr. et al. | |
| 2004/0059333 A1 | 3/2004 | Carl et al. | |
| 2004/0082954 A1 | 4/2004 | Teitelbaum et al. | |
| 2004/0082960 A1 | 4/2004 | Davison | |
| 2004/0082961 A1 | 4/2004 | Teitelbaum | |
| 2004/0087950 A1 | 5/2004 | Teitelbaum | |
| 2004/0092934 A1 | 5/2004 | Howland | |
| 2004/0093001 A1 | 5/2004 | Hamada | |
| 2004/0106934 A1 | 6/2004 | Grossman | |
| 2004/0133201 A1 | 7/2004 | Shluzas et al. | |
| 2004/0138662 A1 | 7/2004 | Landry et al. | |
| 2004/0143265 A1 | 7/2004 | Landry et al. | |
| 2004/0143268 A1 | 7/2004 | Falahee | |
| 2004/0147928 A1 | 7/2004 | Landry et al. | |
| 2004/0147936 A1 | 7/2004 | Rosenberg et al. | |
| 2004/0172022 A1 | 9/2004 | Landry et al. | |
| 2004/0176763 A1 | 9/2004 | Foley et al. | |
| 2004/0194791 A1 | 10/2004 | Sterman et al. | |
| 2004/0215190 A1 | 10/2004 | Nguyen et al. | |
| 2004/0215193 A1 | 10/2004 | Shaolian et al. | |
| 2004/0236317 A1 | 11/2004 | Davison | |
| 2004/0254576 A1 | 12/2004 | Dunbar, Jr. et al. | |
| 2004/0260287 A1 | 12/2004 | Ferree | |
| 2004/0267279 A1 | 12/2004 | Casutt et al. | |
| 2005/0010220 A1 | 1/2005 | Casutt et al. | |
| 2005/0010221 A1 | 1/2005 | Dalton | |
| 2005/0021030 A1 | 1/2005 | Pagliuca et al. | |
| 2005/0021031 A1 | 1/2005 | Foley et al. | |
| 2005/0033297 A1 | 2/2005 | Davison | |
| 2005/0038432 A1 | 2/2005 | Shaolian et al. | |
| 2005/0038434 A1 | 2/2005 | Mathews | |
| 2005/0043741 A1 | 2/2005 | Michelson | |
| 2005/0043742 A1 | 2/2005 | Bruneau et al. | |
| 2005/0059969 A1 | 3/2005 | McKinley | |
| 2005/0065515 A1 | 3/2005 | Jahng | |
| 2005/0065517 A1 | 3/2005 | Chin | |
| 2005/0070917 A1 | 3/2005 | Justis | |
| 2005/0080418 A1 | 4/2005 | Simonson et al. | |
| 2005/0085813 A1 | 4/2005 | Spitler et al. | |
| 2005/0090822 A1 | 4/2005 | DiPoto | |
| 2005/0090833 A1 | 4/2005 | DiPoto | |
| 2005/0113833 A1 | 5/2005 | Davison | |
| 2005/0124991 A1 | 6/2005 | Jahng | |
| 2005/0131407 A1 | 6/2005 | Sicvol et al. | |
| 2005/0131408 A1 | 6/2005 | Sicvol et al. | |
| 2005/0131421 A1 | 6/2005 | Anderson et al. | |
| 2005/0131422 A1 | 6/2005 | Anderson et al. | |
| 2005/0137461 A1 | 6/2005 | Marchek et al. | |
| 2005/0137593 A1 | 6/2005 | Gray et al. | |
| 2005/0149022 A1 | 7/2005 | Shaolian et al. | |
| 2005/0149035 A1 | 7/2005 | Pimenta et al. | |
| 2005/0154389 A1 | 7/2005 | Selover et al. | |
| 2005/0171540 A1 | 8/2005 | Lim et al. | |
| 2005/0182410 A1 | 8/2005 | Jackson | |
| 2005/0192570 A1 | 9/2005 | Jackson | |
| 2005/0228382 A1 * | 10/2005 | Richelsoph | A61B 17/7041 606/272 |
| 2005/0245928 A1 | 11/2005 | Colleran et al. | |
| 2005/0251139 A1 | 11/2005 | Roh | |
| 2005/0277934 A1 | 12/2005 | Vardiman | |
| 2005/0277942 A1 | 12/2005 | Kullas et al. | |
| 2006/0030839 A1 | 2/2006 | Park et al. | |
| 2006/0030858 A1 | 2/2006 | Simonson et al. | |
| 2006/0030861 A1 | 2/2006 | Simonson et al. | |
| 2006/0111713 A1 | 5/2006 | Jackson | |
| 2006/0111714 A1 | 5/2006 | Foley | |
| 2006/0200135 A1 | 9/2006 | Sherman et al. | |
| 2006/0217735 A1 | 9/2006 | MacDonald et al. | |
| 2006/0247658 A1 | 11/2006 | Pond, Jr. et al. | |
| 2006/0264934 A1 | 11/2006 | Fallin | |
| 2006/0264962 A1 | 11/2006 | Chin et al. | |
| 2006/0293680 A1 | 12/2006 | Jackson | |
| 2007/0043359 A1 | 2/2007 | Altarac et al. | |
| 2007/0083210 A1 | 4/2007 | Hestad et al. | |

(56) References Cited

U.S. PATENT DOCUMENTS

| | | | |
|---|---|---|---|
| 2007/0093824 A1 | 4/2007 | Hestad et al. | |
| 2007/0288026 A1* | 12/2007 | Shluzas | A61B 17/02 606/86 A |
| 2008/0009864 A1 | 1/2008 | Forton et al. | |
| 2008/0312696 A1* | 12/2008 | Butters | A61B 17/7037 606/264 |
| 2009/0062858 A1* | 3/2009 | Dziedzic | A61B 17/7089 606/278 |
| 2009/0062864 A1* | 3/2009 | Ludwig | A61B 17/705 606/301 |
| 2009/0216328 A1 | 8/2009 | Birkmeyer et al. | |
| 2009/0222044 A1* | 9/2009 | Gorek | A61B 17/0218 606/279 |
| 2009/0228056 A1 | 9/2009 | Jackson | |
| 2009/0270916 A1* | 10/2009 | Ramsay | A61B 17/1735 606/246 |
| 2010/0137915 A1 | 6/2010 | Anderson et al. | |
| 2010/0168796 A1* | 7/2010 | Eliasen | A61B 17/7035 606/264 |
| 2010/0211100 A1* | 8/2010 | Mack | A61B 17/7037 606/246 |
| 2010/0241172 A1* | 9/2010 | Biyani | A61B 17/7032 606/279 |
| 2010/0249844 A1* | 9/2010 | Durrani | A61B 17/025 606/259 |
| 2010/0292739 A1* | 11/2010 | Schwab | A61B 17/7032 606/305 |
| 2010/0331901 A1 | 12/2010 | Iott et al. | |
| 2011/0015678 A1 | 1/2011 | Jackson | |
| 2011/0077692 A1 | 3/2011 | Jackson | |
| 2011/0152940 A1 | 6/2011 | Frigg et al. | |
| 2011/0238120 A1 | 9/2011 | Chin | |
| 2011/0245877 A1* | 10/2011 | Pisharodi | A61B 17/7001 606/268 |
| 2011/0245884 A9 | 10/2011 | Brumfield et al. | |
| 2012/0089191 A1 | 4/2012 | Altarac et al. | |
| 2012/0123477 A1 | 5/2012 | Landry et al. | |
| 2012/0158070 A1 | 6/2012 | Jackson | |
| 2012/0197302 A1 | 8/2012 | Fallin | |
| 2012/0209332 A1* | 8/2012 | Janowski | A61B 17/7038 606/278 |
| 2013/0072991 A1* | 3/2013 | Rathbun | A61B 17/7037 606/305 |
| 2013/0079827 A1* | 3/2013 | Neary | A61B 17/7077 606/264 |
| 2013/0090691 A1* | 4/2013 | Zhang | A61B 17/7001 606/264 |
| 2014/0107706 A1* | 4/2014 | McClintock | A61B 17/7002 606/264 |

FOREIGN PATENT DOCUMENTS

| | | | |
|---|---|---|---|
| AT | 169811 | 9/1998 | |
| AT | 173600 | 12/1998 | |
| AT | 185062 | 10/1999 | |
| AU | 3838789 | 1/1990 | |
| AU | 648047 | 5/1991 | |
| AU | 6534790 | 5/1991 | |
| AU | 645780 | 9/1991 | |
| AU | 7251191 | 9/1991 | |
| AU | 653997 | 10/1992 | |
| AU | 1384192 | 10/1992 | |
| AU | 683243 | 8/1994 | |
| AU | 6089394 | 8/1994 | |
| AU | 6899996 | 3/1997 | |
| AU | 695006 | 10/1997 | |
| AU | 2877297 | 10/1997 | |
| BG | 60286 | 4/1994 | |
| CA | 2072992 | 5/1991 | |
| CA | 2051408 | 8/1991 | |
| CA | 1306913 | 9/1992 | |
| CA | 2064277 | 9/1992 | |
| CA | 2155422 | 8/1994 | |
| CA | 1332999 | 11/1994 | |
| CA | 2571467 A1 * | 1/2006 | A61B 17/7088 |
| CA | 2859280 A1 * | 6/2013 | A61B 17/7035 |
| CH | KR 20080035999 A * | 4/2008 | A61B 17/7088 |
| DE | 3711091 A1 | 10/1988 | |
| DE | 4238339 A1 | 5/1994 | |
| DE | 69026067 | 10/1996 | |
| DE | 29710979 U1 | 8/1997 | |
| DE | 68928675 | 10/1998 | |
| DE | 69225521 | 10/1998 | |
| DE | 19726754 A1 | 2/1999 | |
| DE | 68928790 | 3/1999 | |
| DE | 69032788 | 5/1999 | |
| DE | 69420947 | 5/2000 | |
| DE | 10027988 A1 | 1/2002 | |
| DK | 0441084 | 12/1990 | |
| DK | 0506420 | 3/1992 | |
| EP | 0369603 | 5/1990 | |
| EP | 0419564 | 4/1991 | |
| EP | 0441084 | 8/1991 | |
| EP | 0498816 | 8/1992 | |
| EP | 0506420 | 9/1992 | |
| EP | 0528177 A2 | 2/1993 | |
| EP | 0665731 | 8/1995 | |
| EP | 0683651 | 11/1995 | |
| EP | 0712607 | 5/1996 | |
| EP | 0955894 | 11/1999 | |
| EP | 1374786 A2 | 1/2004 | |
| EP | 1468652 A1 | 10/2004 | |
| EP | 1545355 B1 | 12/2008 | |
| ES | 2086391 | 8/1991 | |
| ES | 2124217 | 8/1992 | |
| ES | 2117968 | 9/1992 | |
| ES | 2141217 | 11/1995 | |
| ES | WO 0228299 A1 * | 4/2002 | A61B 17/7007 |
| FI | 102512 | 8/1991 | |
| FI | 906130 | 8/1991 | |
| FR | 2657775 | 8/1991 | |
| FR | 2677242 A1 * | 12/1992 | A61B 17/7086 |
| GR | 3020170 | 9/1996 | |
| HK | 1005540 | 9/2000 | |
| HU | 209422 | 8/1992 | |
| IE | 904456 | 12/1990 | |
| IE | 74188 | 7/1997 | |
| JP | H02149271 | 10/1989 | |
| JP | 2551670 | 6/1990 | |
| JP | 2554298 | 12/1992 | |
| JP | H04506923 | 12/1992 | |
| JP | H06142115 | 5/1994 | |
| JP | H08506501 | 7/1996 | |
| JP | H05501507 | 4/1998 | |
| JP | H11511357 | 10/1999 | |
| JP | 2003511190 A | 3/2003 | |
| JP | 2006504505 A | 2/2006 | |
| KR | 970009551 | 6/1997 | |
| NO | 180322 | 8/1991 | |
| NO | 921773 | 7/1992 | |
| NO | 180322 | 4/1997 | |
| PT | 96202 | 9/1991 | |
| RO | 107081 | 9/1993 | |
| RU | 2043081 | 9/1995 | |
| SU | 839513 | 6/1981 | |
| TR | 25016 | 9/1992 | |
| WO | WO8912431 | 12/1989 | |
| WO | WO9106261 | 5/1991 | |
| WO | WO9111967 | 8/1991 | |
| WO | WO9116020 | 10/1991 | |
| WO | WO9318722 | 9/1993 | |
| WO | WO9409726 | 5/1994 | |
| WO | WO9417759 | 8/1994 | |
| WO | WO9514437 | 6/1995 | |
| WO | WO9714457 | 4/1997 | |
| WO | WO9707743 | 6/1997 | |
| WO | WO9822030 A1 | 5/1998 | |
| WO | WO9836785 | 8/1998 | |
| WO | WO0045720 | 8/2000 | |
| WO | WO0112080 A1 | 2/2001 | |
| WO | WO0137744 A2 | 5/2001 | |
| WO | WO0141681 A1 | 6/2001 | |

(56) References Cited

FOREIGN PATENT DOCUMENTS

| | | |
|---|---|---|
| WO | WO0160234 A2 | 8/2001 |
| WO | WO0160263 A1 | 8/2001 |
| WO | WO0160270 A1 | 8/2001 |
| WO | WO0195823 A1 | 12/2001 |
| WO | WO0228299 | 4/2002 |
| WO | WO03020110 A2 | 3/2003 |
| WO | WO03037170 A2 | 5/2003 |
| WO | WO03057055 A1 | 7/2003 |
| WO | WO03028566 A1 | 10/2003 |
| WO | WO03079914 A1 | 10/2003 |
| WO | WO03088810 A2 | 10/2003 |
| WO | WO03088878 A1 | 10/2003 |
| WO | WO2004004584 A1 | 1/2004 |
| WO | WO2004017847 A2 | 3/2004 |
| WO | WO2004021899 A1 | 3/2004 |
| WO | WO2004028382 A2 | 4/2004 |
| WO | WO2004037070 A2 | 5/2004 |
| WO | WO2004037074 A2 | 5/2004 |
| WO | WO2004041100 A1 | 5/2004 |
| WO | WO2004058045 A2 | 7/2004 |
| WO | WO2004080318 A1 | 9/2004 |
| WO | WO2005018466 A2 | 3/2005 |
| WO | WO2005023123 A1 | 3/2005 |
| WO | WO2005032358 A2 | 4/2005 |
| WO | WO2005060534 A2 | 7/2005 |
| WO | WO 2006057837 A1 * | 6/2006 ......... A61B 17/7037 |
| WO | WO2006116662 A1 | 11/2006 |
| WO | WO2006125029 A2 | 11/2006 |
| WO | WO 2016094588 A2 * | 6/2016 ......... A61B 17/7037 |

OTHER PUBLICATIONS

Office Action from U.S. Appl. No. 10/868,075, dated Mar. 24, 2008.
Office Action from U.S. Appl. No. 10/868,075, dated Mar. 9, 2009.
Office Action from U.S. Appl. No. 11/178,035, dated May 1, 2008.
Office Action from U.S. Appl. No. 11/178,035, dated Sep. 5, 2008.
Office Action from U.S. Appl. No. 11/178,035, dated Mar. 4, 2009.
Office Action from U.S. Appl. No. 11/178,035, dated Nov. 13, 2009.
Office Action from U.S. Appl. No. 11/202,487, dated Dec. 9, 2008.
Office Action from U.S. Appl. No. 11/202,487, dated Aug. 5, 2009.
Office Action from U.S. Appl. No. 12/316,637, dated Oct. 17, 2011.

* cited by examiner

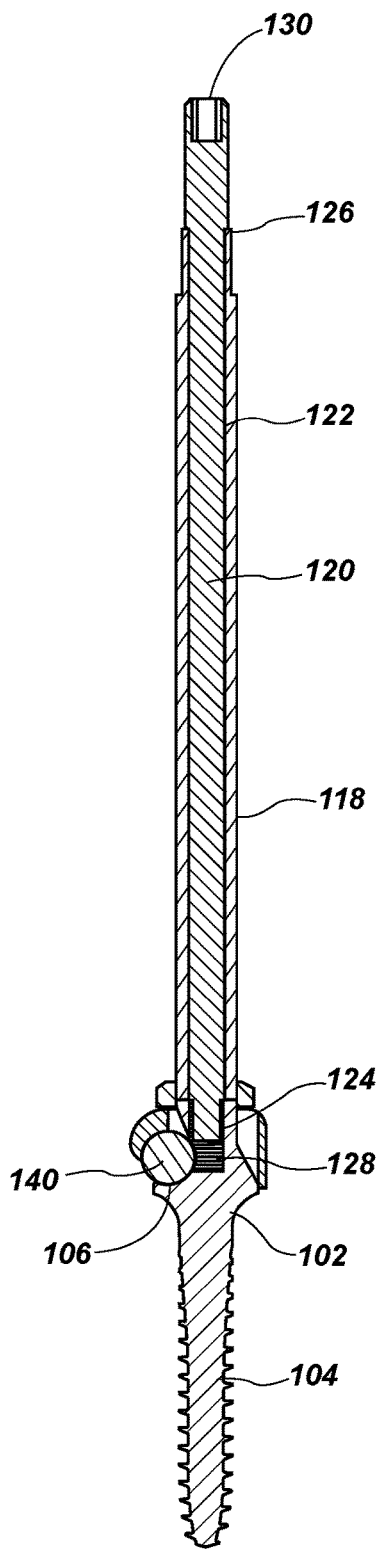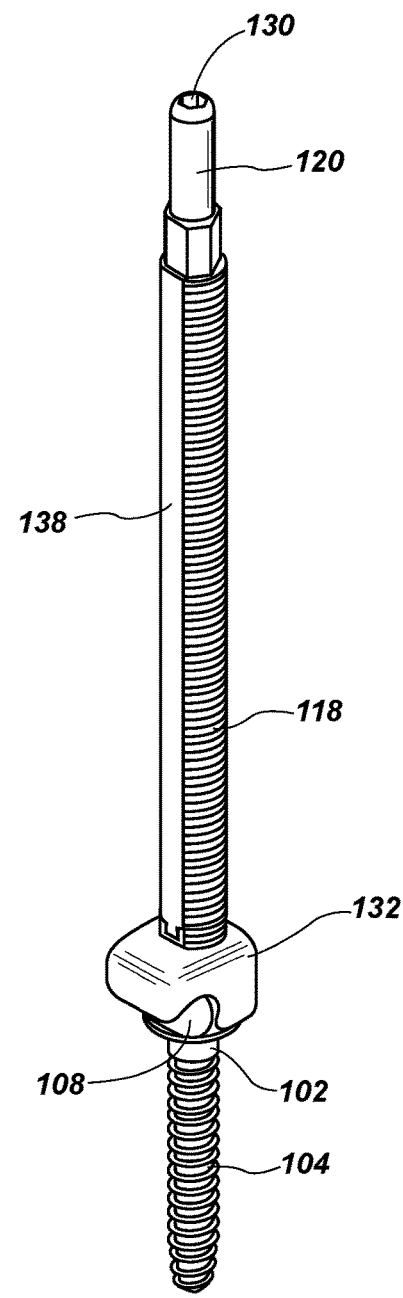
FIG. 9
FIG. 10

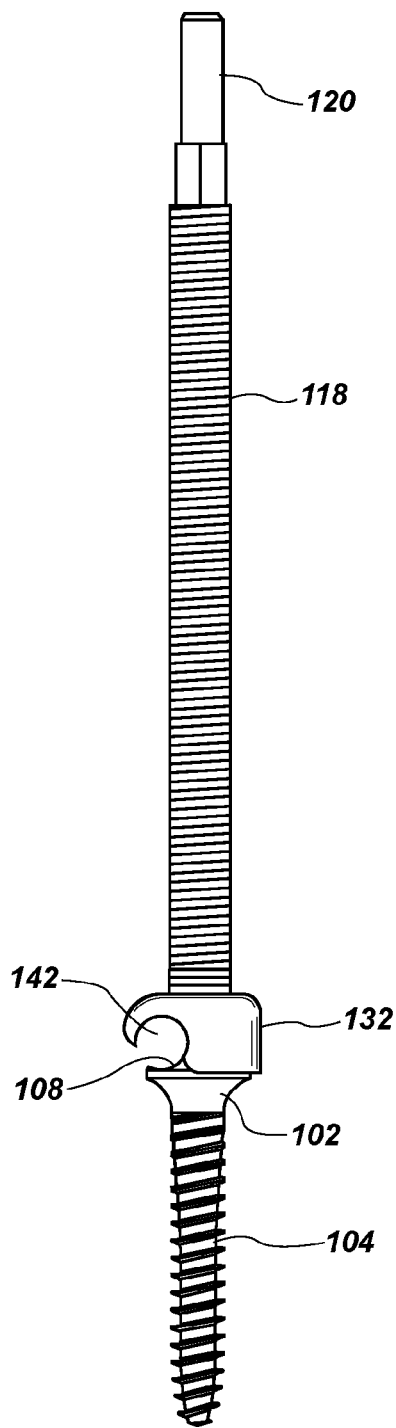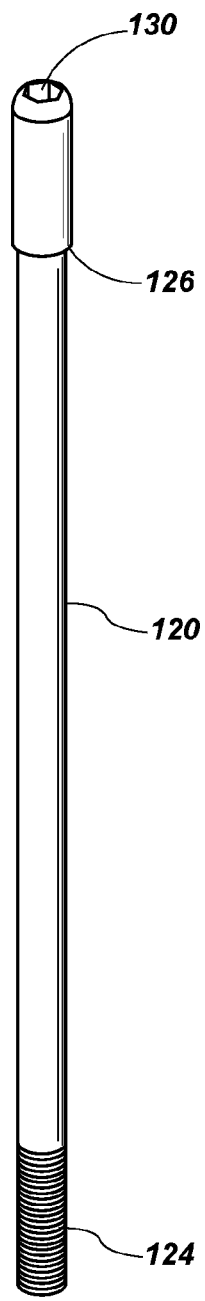
FIG. 11
FIG. 12

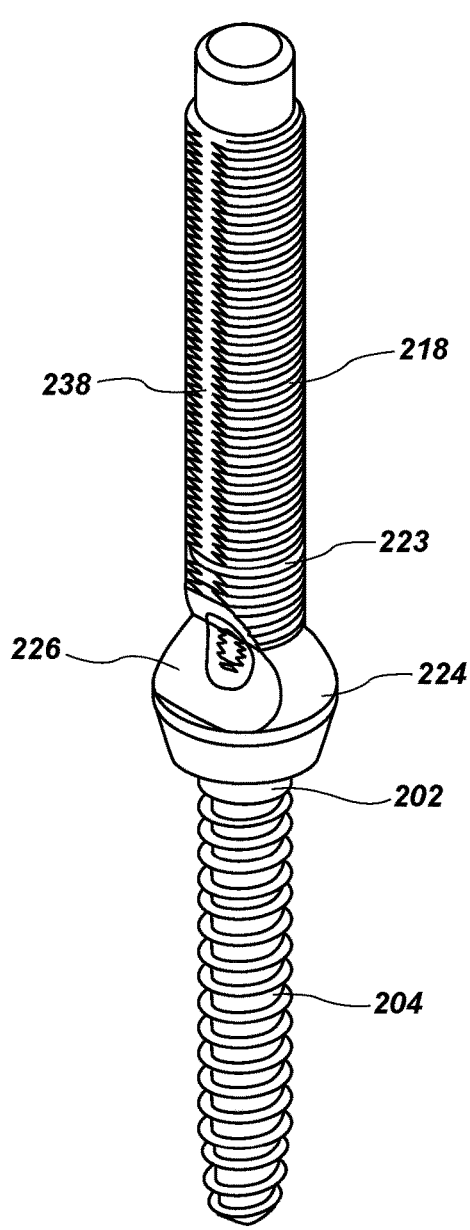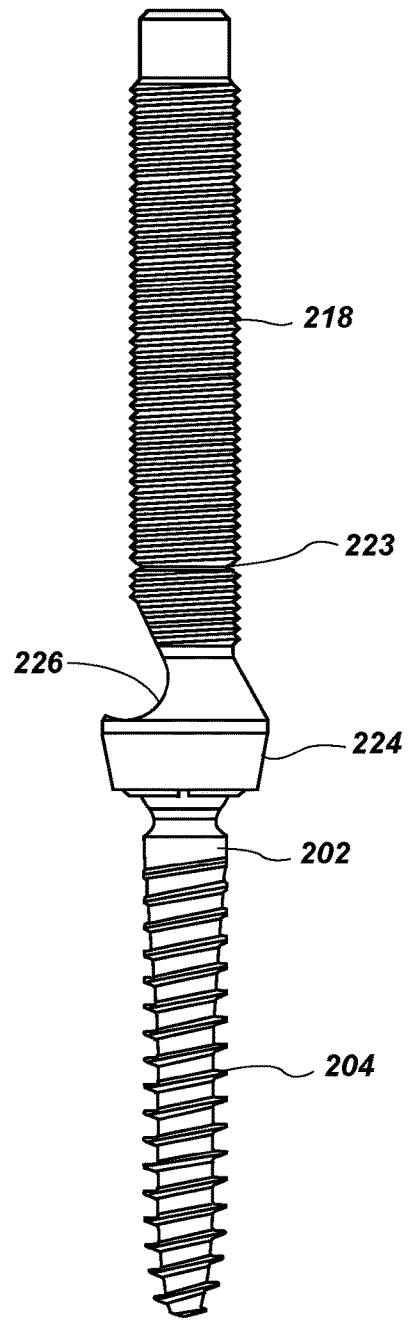
FIG. 19
FIG. 20

SPINE ALIGNMENT SYSTEM

STATEMENT REGARDING FEDERALLY SPONSORED RESEARCH OR DEVELOPMENT

This application claims the benefit of U.S. Provisional Application No. 62/089,725, filed Dec. 9, 2014, and U.S. Provisional Application No. 62/180,870, filed Jun. 17, 2015, which are hereby incorporated by reference herein in their entirety, including but not limited to those portions that specifically appear hereinafter, the incorporation by reference being made with the following exception: in the event that any portion of the above-referenced applications are inconsistent with this application, this application supercedes said above-referenced applications.

BACKGROUND

The Field of the Present Disclosure

The present disclosure relates generally to spinal alignment and stabilization devices.

Description of Related Art

Curvature and deformities of the spine impact many people and can have serious, and even life-threatening, health consequences. Beneficially, curvature and deformities of the spine can often be treated various procedures, including spinal fusion surgery, which permanently connects two or more vertebrae in a spine, eliminating motion between them. This type of spinal fusion can improve stability of the spine while also correcting deformities, reducing pain and improving the life qualify of a patient. Spinal fusion often involves placing a bone graft in the space between two spinal vertebrae.

A surgeon may use plates, screws or rods to hold the vertebrae and graft in place to promote healing after spinal fusion. Once the bone graft heals, the vertebrae are permanently connected.

Bony anchors or screws are commonly used to secure the vertebrae to a longitudinal alignment rod. These may connect multiple level anchors. Typically, two alignment rods are utilized between each level, one on each side of the spinous process. However, conventional spine alignment devices are characterized by being overly complex, needing numerous individual parts and tools for assembly and installation.

Conventional alignment devices are thus characterized by several disadvantages that are addressed by the present disclosure. The present disclosure minimizes, and in some aspects eliminates, the above-mentioned failures, and other problems, by utilizing the methods and structural features described herein.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims. An understanding of the present disclosure will provide an appreciation of the unique and beneficial combination of the engineering sciences and the medical sciences which result in heretofore unavailable advantages.

BRIEF DESCRIPTION OF THE DRAWINGS

The features and advantages of the disclosure will become apparent from a consideration of the subsequent detailed description presented in connection with the accompanying drawings in which:

FIG. 9 is an assembled, cross-sectional side view of the embodiment of FIG. 1;

FIG. 10 is an assembled perspective view of the embodiment of FIG. 1, as illustrated in FIG. 9, shown without an alignment rod;

FIG. 11 is an assembled side view of the embodiment of FIG. 1 without an alignment rod;

FIG. 12 is a perspective view of an inner rod of the embodiment of FIG. 1;

FIG. 19 is an assembled perspective view of the embodiment of FIG. 15;

FIG. 20 is an assembled side view of the embodiment of FIG. 15;

DETAILED DESCRIPTION

Figure 1:
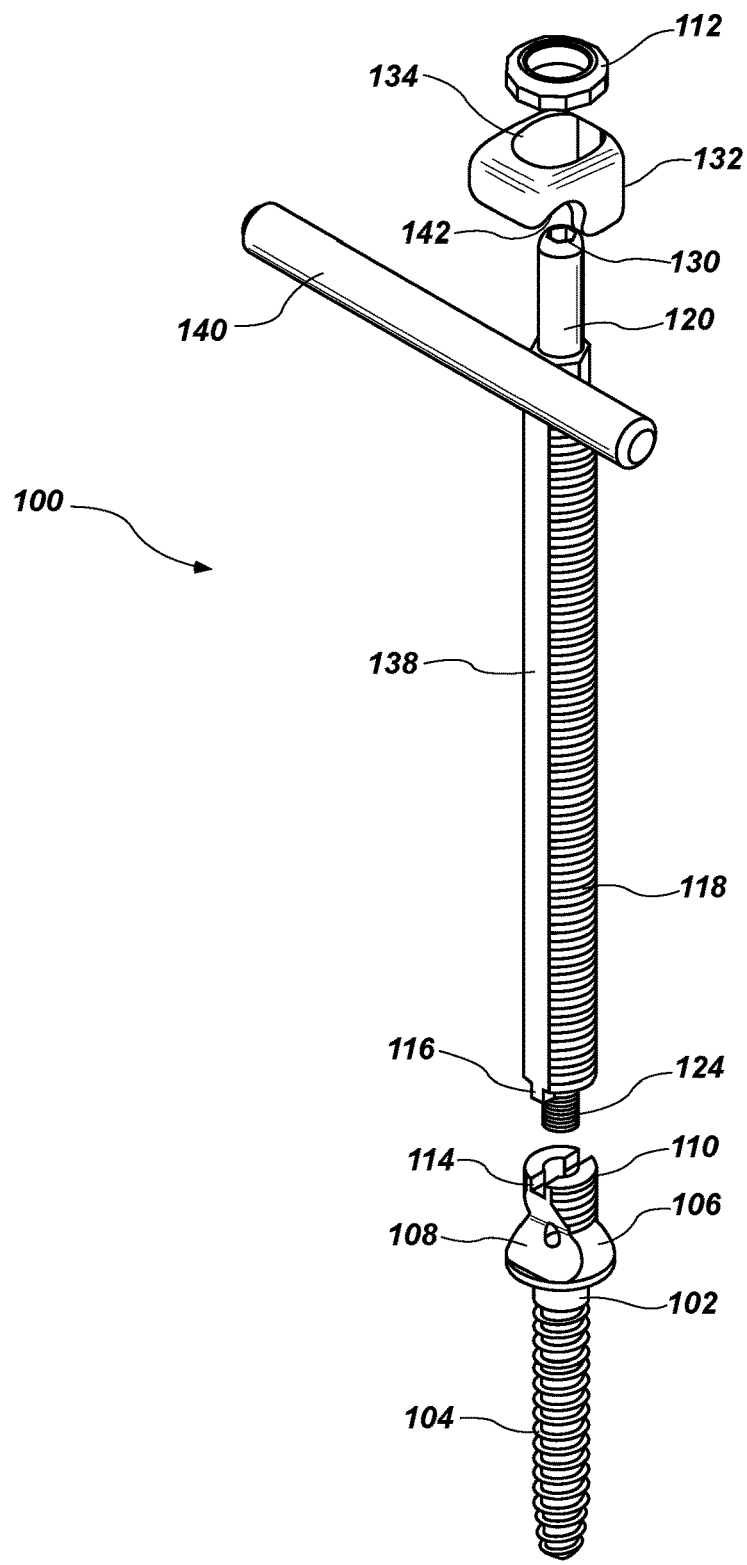
FIG. 1 is an exploded perspective view of a mono-axial embodiment of the present disclosure.
Figure 2:
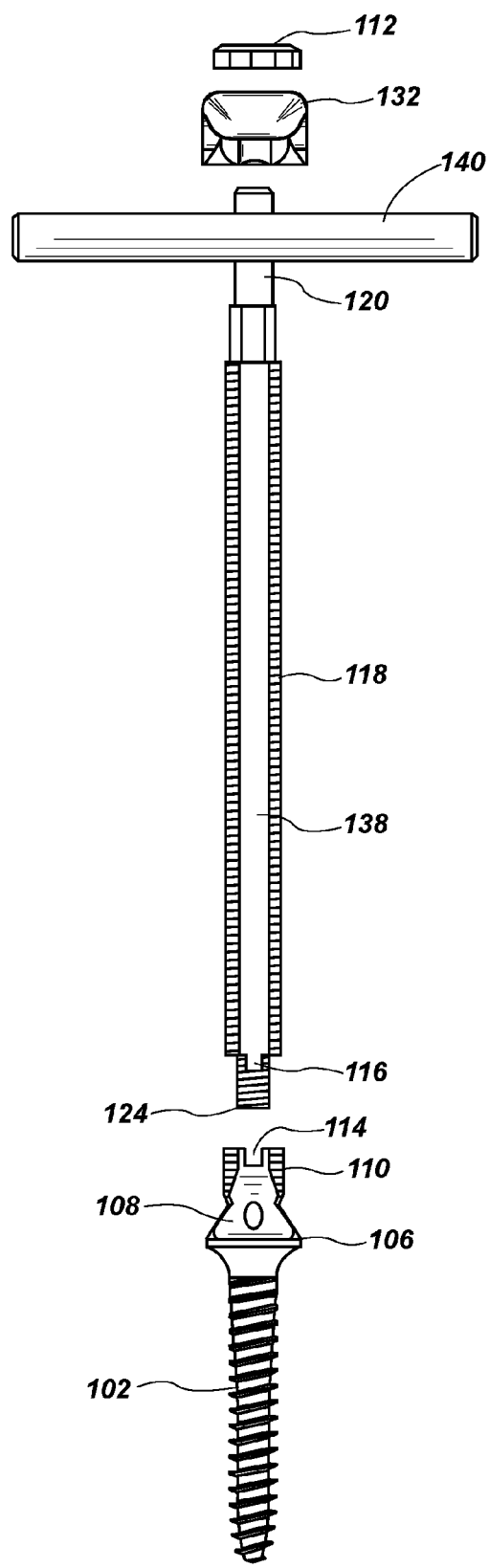
FIG. 2 is an exploded front view of the embodiment of FIG. 1.
Figure 3:
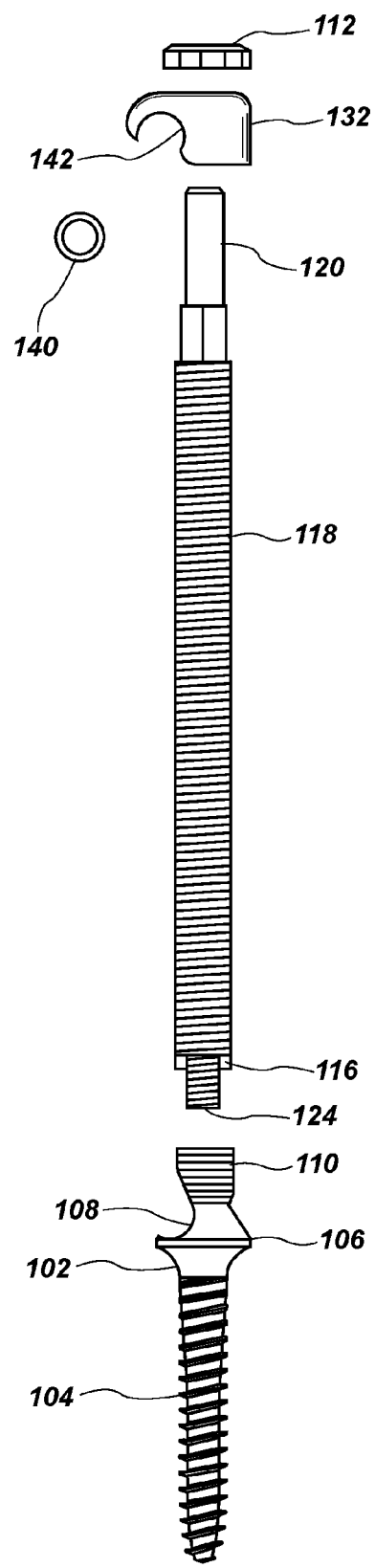
FIG. 3 is an exploded side view of the embodiment of FIG. 1.
Figure 4:
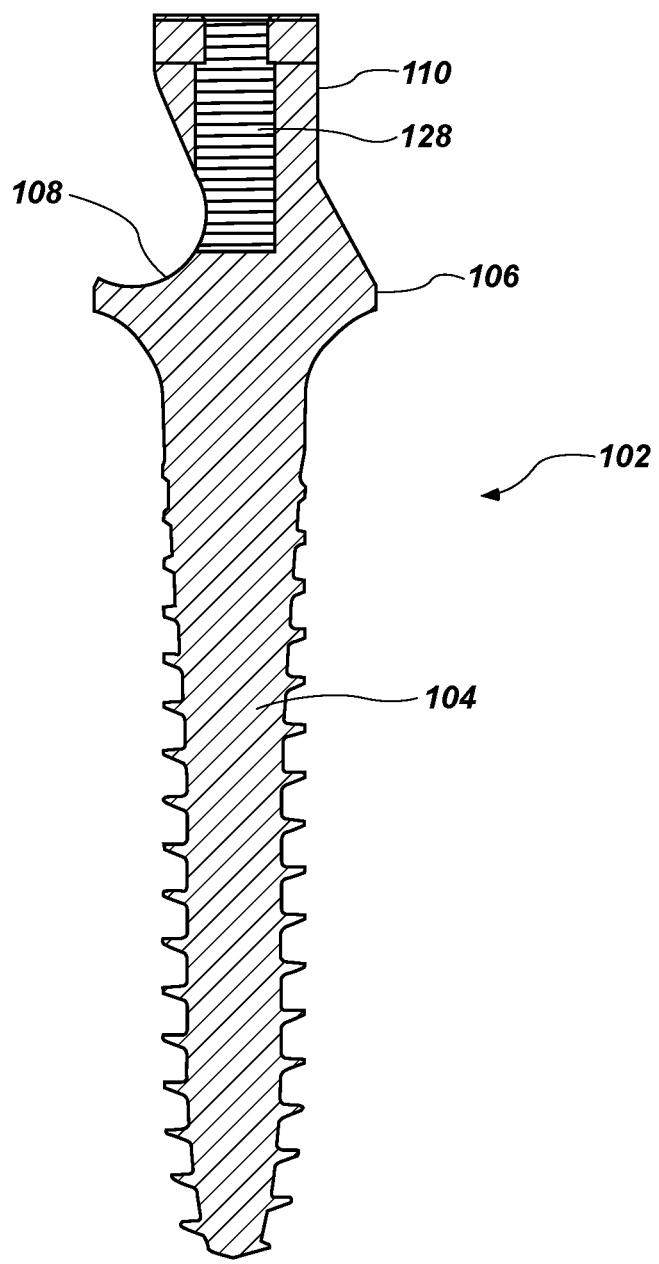
FIG. 4 is a cross-sectional view of a mono-axial pedicle screw of the embodiment of FIG. 1.
Figure 5:
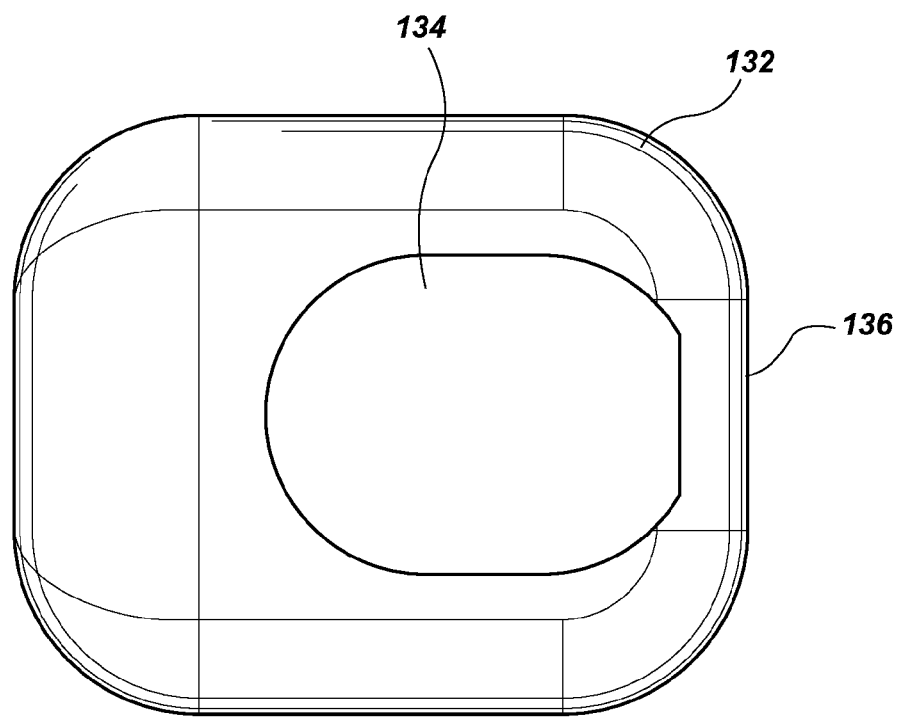
FIG. 5 is a top view of a cap of the embodiment of FIG. 1.
Figure 5A:
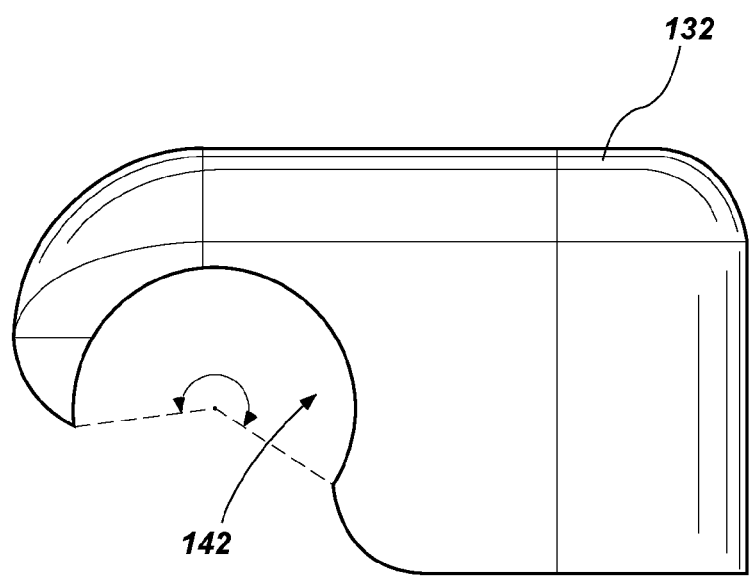
FIG. 5a is a side view of the cap if the embodiment of FIG. 1.
Figure 6:
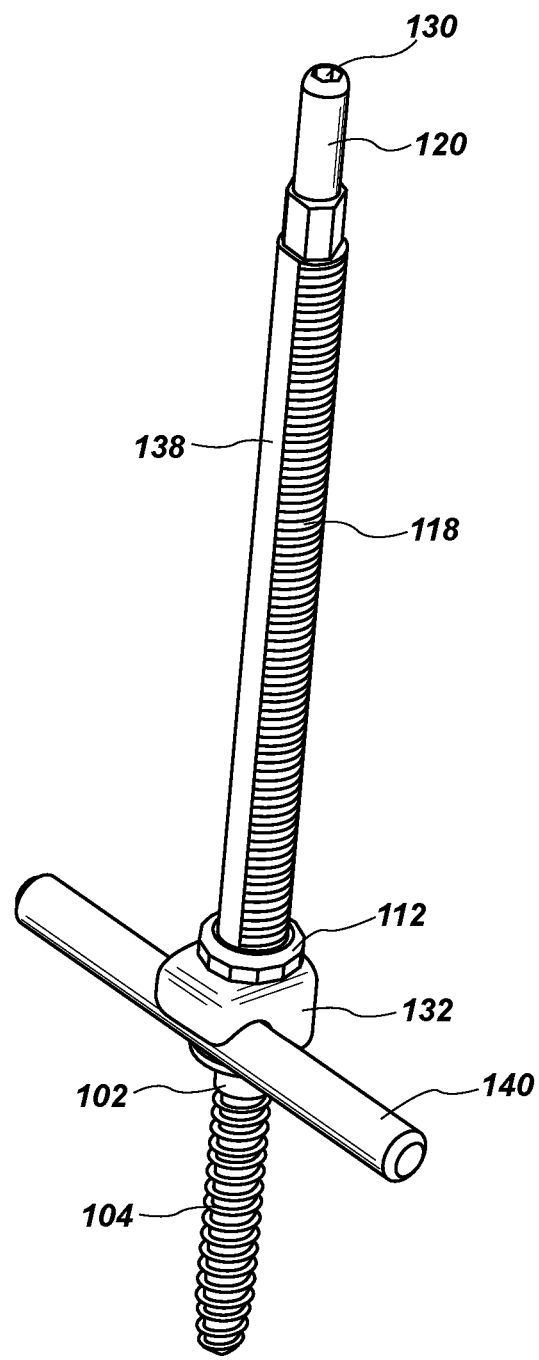
FIG. 6 is an assembled perspective view of the embodiment of FIG. 1.
Figure 7:
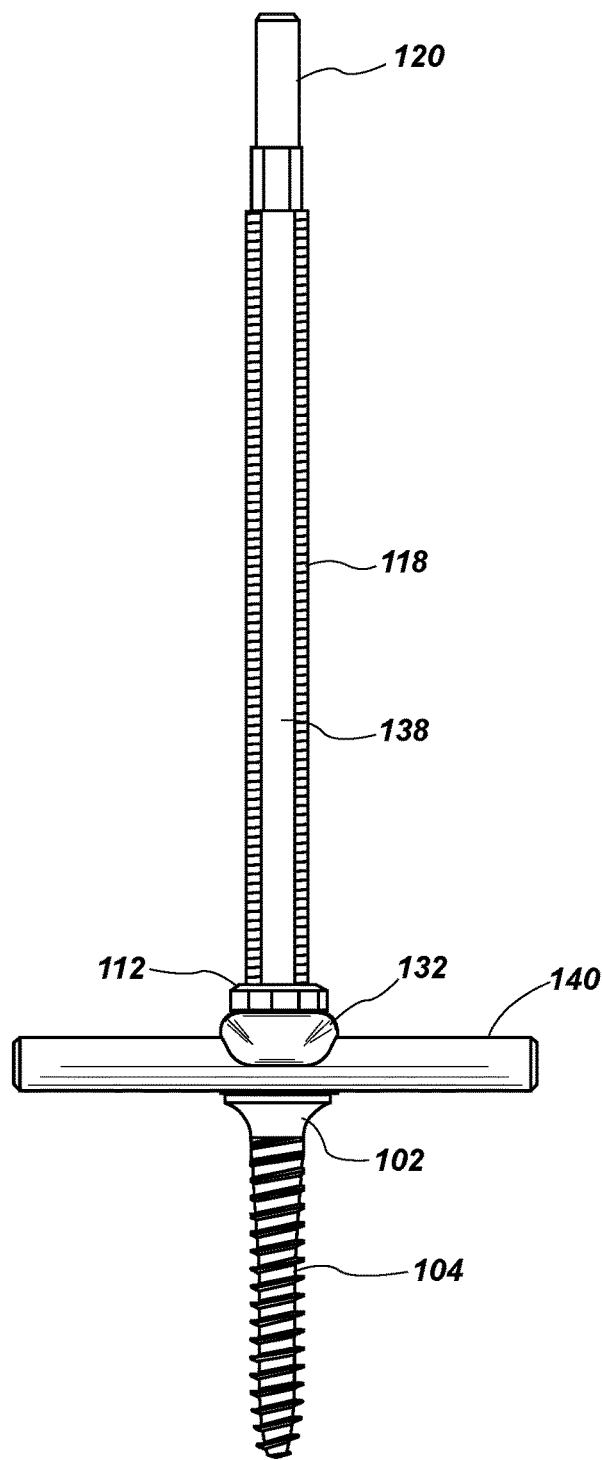
FIG. 7 is an assembled front view of the embodiment of FIG. 1.
Figure 8:
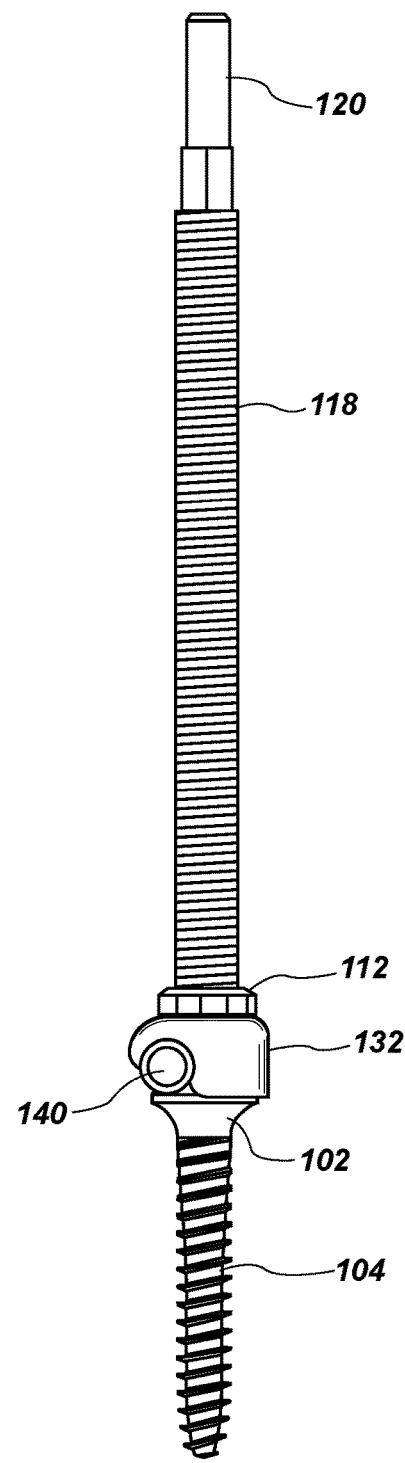
FIG. 8 is an assembled side view of the embodiment of FIG. 1.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

Applicant has discovered a novel apparatus and method for aligning, stabilizing and securing adjacent spinal vertebrae using a spine alignment system utilizing side loading and incremental reduction of adjacent spinal vertebrae to an alignment rod. This means that an alignment rod can be captured into a side of the a corresponding pedicle screw, as opposed to capturing the alignment rod on top of the pedicle screw.

FIGS. 1-14 illustrate an spine alignment system 100 according to a first embodiment of the current disclosure. The spine alignment system 100 includes a mono-axial, or fixed axis, pedicle screw 102. The pedicle screw 102 includes a threaded shaft 104 which facilitates insertion and fixation into the bony pedicle of a vertebral body. The threaded shaft 104 may have a fixed or tapered diameter, with single or multiple start threads which may be spaced between 1 mm and 3 mm apart, for example.

The pedicle screw 102 includes a head 106 having a generally conical shape. The head 106 includes an approximately C-shaped cut-out portion 108, or slot, located substantially on a side of the head 106. The slot 108 includes a longitudinal axis that is substantially perpendicular to the longitudinal axis of the pedicle screw 102. The conical shape of the head 106 converts to a cylindrical shape above the slot 108, resulting in a cylindrical portion 110. The cylindrical portion 110 includes an exterior thread configured to receive a locking nut 112.

The cylindrical portion 110 of the head 106 can also include a key slot 114 configured to receive a key 116 of an extension shaft 118. The extension shaft 118 includes external threads that are formed to match the threads on the cylindrical portion 110 of the head 106. When the key 116 of the extension shaft 118 is received into the key slot 114, the threads of the extension shaft 118 will perfectly match the threads of the cylindrical portion 110 of the head 106, such that the locking nut 112 can threadedly engage the extension shaft 118 and the cylindrical portion 110 of the head 106.

An inner rod 120 is substantially cylindrical in shape and is configured to be received within a longitudinal throughhole 122 in the extension rod 118, as shown in FIG. 10. The inner rod 120 includes a threaded distal end 124 and a stepped portion 126 near the proximal portion of the inner rod 120. The threaded distal end 124 is configured to threadedly engage a threaded bore 128 within the head 106 of the pedicle screw 102. The stepped portion 126 of the inner rod 120 is configured to abut against the proximal end of the extension shaft 118, which thereby secures the extension shaft 118 to the head 106 of the pedicle screw 102.

In another embodiment, the extension shaft 118 can be integrated with the head 106 of the pedicle crew 102 with a fracture groove cut into a distal end of the extension shaft 118, which can enable the extension shaft 118 to break-away from the head 106 of the pedicle screw 102 after installation of the spine alignment system 100.

Once the inner rod 120 has secured the extension shaft 118 to the pedicle screw 102, a surgeon or user can insert or screw the pedicle screw 102 into the bony pedicle of a vertebra. The inner rod 120 includes a head 130, which can be configured to receive a drill attachment, or manual driver attachment, which can help facilitate the driving or screwing of the pedicle screw 102 into the bony pedicle of a vertebra.

The extension shaft 118 is configured to receive a cap 132. The cap 132 includes an oblong through-hole 134 that includes a substantially flat side surface 136 that is configured to lie flat against a flat side surface 138 of the extension shaft 118. The extension shaft 118 includes a pair of opposing flat side surfaces 138, one of the pair of flat surfaces 138 faces the same direction as the slot 108 of the pedicle screw 102. These flat side surfaces 138 serve as a guide for the cap 132 after capturing an alignment rod 140 and translating down the length of the extension shaft 118. The alignment rod 140 is captured by the cap 132 within an approximately C-shaped cutout 142, or slot, that is formed and dimensioned to substantially the same diameter as the alignment rod 140.

One of the pair of flat surfaces 138 engages the alignment rod 140, pressing against the alignment rod 140 while the alignment rod is engaged within the slot 142, helping secure the alignment rod 140 in place during axial translation of the cap 132. The opposing flat surface 138 of the extension shaft will engage the flat surface 136 within the cap 132, creating substantially co-planar contact between the two surfaces resulting a rotationally locked engagement, helping to prevent unwanted rotation of the cap 132 during axial translation down the extension shaft 118.

The cap 132 may also be configured to form the slot 142 with an arc length angle of $\theta$, where $\theta$ may be greater than 180 degrees. The slot 142 having an arc length angle of greater that 180 degrees enables the slot to receive the alignment rod 140 with a snap-fit engagement. The small flexibility of the cap material allows the slot 142 to deform enough to allow the alignment rod to be received therein, then retain the alignment rod 140 within the slot 140. Alternative cap embodiments may also include a slot having an arc length angle that is 180 degree, or less than 180 degrees.

During assembly and use, a surgeon or user will insert and secure the pedicle screw 102, with the adjoined extension shaft 118, to the bony pedicle of a desired vertebra. Once the pedicle screw 102 is secured, the surgeon or user can then place the cap 132 onto the proximal portion of the extension shaft 118.

After the cap 132 is engaged to the extension shaft 118, the surgeon can then capture the alignment rod 140 with the slot 142 of the cap 132. The cap 132 can then carry the alignment rod 140 down the length of the extension shaft 118 until the alignment rod 140 is captured and secured between the slot 142 of the cap 132 and the slot 108 of the head 106 of the pedicle screw 102.

The cap 132 is pushed down the length of the extension shaft 118 by the locking nut 112. The locking nut 112 is threadedly engaged with the extension shaft 118 above the cap 132, such that as the surgeon drives the locking nut 112, the locking nut 112 pushes the cap 132 toward the head 106 of the pedicle screw 102. The surgeon can then drive the locking nut 112 until the cap 132 secures the alignment rod 140 to the head 106.

Once fully secured, as shown in FIGS. 6-9, the slot 142 of the cap 132 and the slot 108 of the head 106 of the pedicle screw 102 will surround the circumference of the alignment rod, although not fully, enough to prevent the alignment rod 140 from breaking away from the pedicle screw 102 in a lateral direction. In an embodiment, the cap 132 deforms around the slot 142 as the nut 112 tightens the cap 132 against the head 106 of the pedicle screw 102. Due to the deformation of the cap 132, the cap 132 cannot be used again after it has been fully secured to the head.

The cylindrical portion 110 of the head 106 has sufficient length to accommodate both the cap 132 and the locking nut 112 when fully secured, such that, the extension shaft 118 can then be removed from the engagement with the pedicle screw 102.

Figure 13:
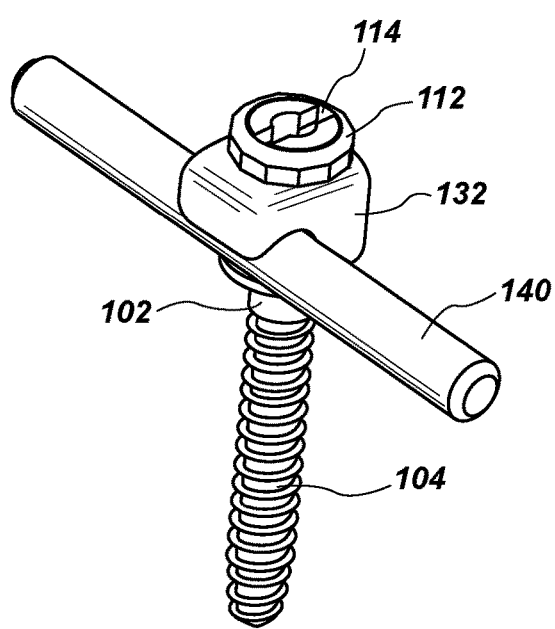
FIG. 13 is an assembled side view of the embodiment of FIG. 1 without an extension shaft.
Figure 14:
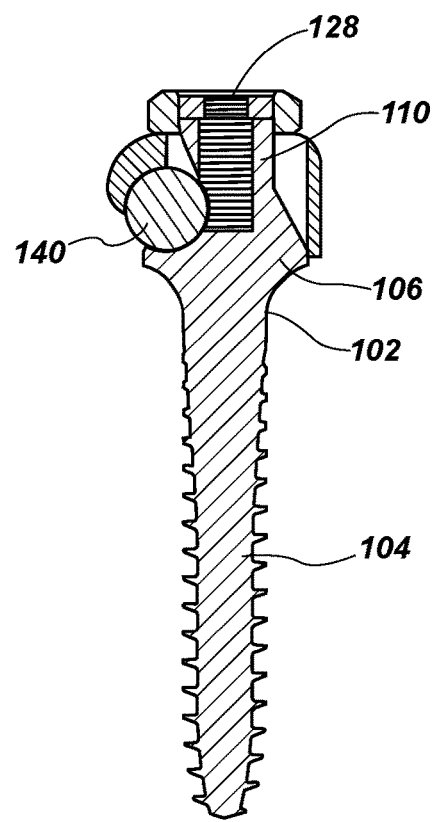
FIG. 14 is an assembled, cross-sectional side view of the embodiment of FIG. 1 without an extension shaft.
Figure 15:
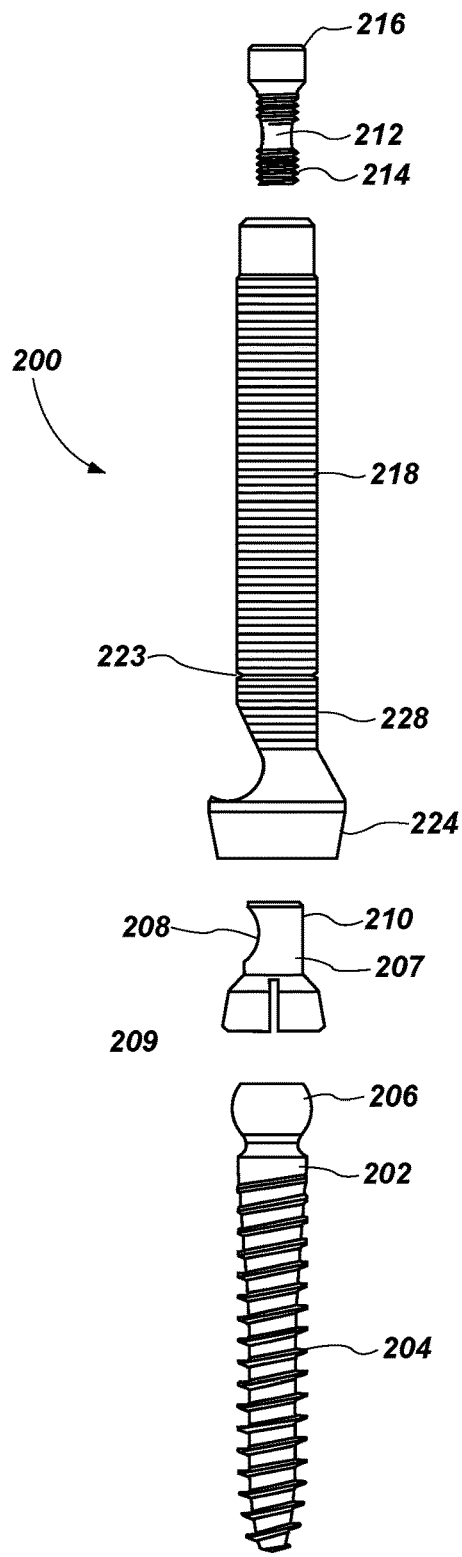
FIG. 15 is an exploded side view of a poly-axial embodiment of the present disclosure.

As shown in FIGS. 13 and 14, the extension shaft 118 can then be disengaged from the pedicle screw 102 by unscrewing the inner rod 120 from the threaded bore 128 within the head 106 of the pedicle screw 102, which will then release the extension shaft 118 from engagement with the pedicle screw 102.

Multiple spine alignment systems 100 can be secured to corresponding vertebra that a surgeon is attempting to set in alignment. Once all of the desired pedicle screws 102 are secured to the corresponding vertebra, caps 132 capturing the alignment rod 140 can be incrementally translated down their corresponding extension shafts 118 until the alignment rod 140 is secured to each of the heads 106 of the pedicle screws 102.

This incremental translation of the caps 132 and alignment rod 140 can provide load sharing across the entire series of pedicle screws 102, decreasing the stress at individual bone-screw interfaces. Additionally, the incremental securement of the alignment rod 140 to the pedicle screws 102 can serve as a reduction tool, bringing all of the desired vertebrae into alignment with the alignment rod 140, thereby reducing the number of tools and steps during a surgical procedure.

Another advantage of the spine alignment system is that a surgeon can drive the pedicle screw 102 and the locking nut 112 with a powered driving instrument, thus removing the need for manual and often laborious tightening and alignment of the alignment rod 140 to the corresponding pedicle screws 102. It will be appreciated that the use of a powered driving instrument, whatever the source of the power, can greatly improve the efficiency of the surgical procedure and thus beneficially reduce the time required to complete the procedure.

FIGS. 15-26 illustrate another embodiment of a spine alignment system 200 of the current disclosure. FIGS. 15-20 illustrate a pedicle screw 202 and extension shaft 218 assembly of the spine alignment system 200. The spine alignment system 200 includes a poly-axial, pedicle screw 202. The pedicle screw 202 includes a threaded shaft which facilitates insertion and fixation into the bony pedicle of a vertebral body. The threaded shaft 204 may have a fixed or tapered diameter, with single or multiple start threads which may be spaced from about 1 mm to about 3 mm apart, for example.

The pedicle screw 102 includes a head 206 having a generally spherical shape. The head 206 is configured to receive a collet 207. The collet is also configured to be received within the bottom, or distal end, of the extension shaft 218. The collet 207 includes an approximately C-shaped cut-out portion 208, or slot, located substantially on a side of the collet 206. The slot 208 includes a longitudinal axis that is substantially perpendicular to the longitudinal axis of the pedicle screw 202.

The collet 207 includes a conical-shaped receiving bore 209 that is configured to receive the head 206 of the pedicle screw 202. The collet 207 includes a cylindrical portion 210 above, or proximal to, the receiving bore 209. The cylindrical portion 210 includes the slot 208 in a side portion thereof.

Figure 16:
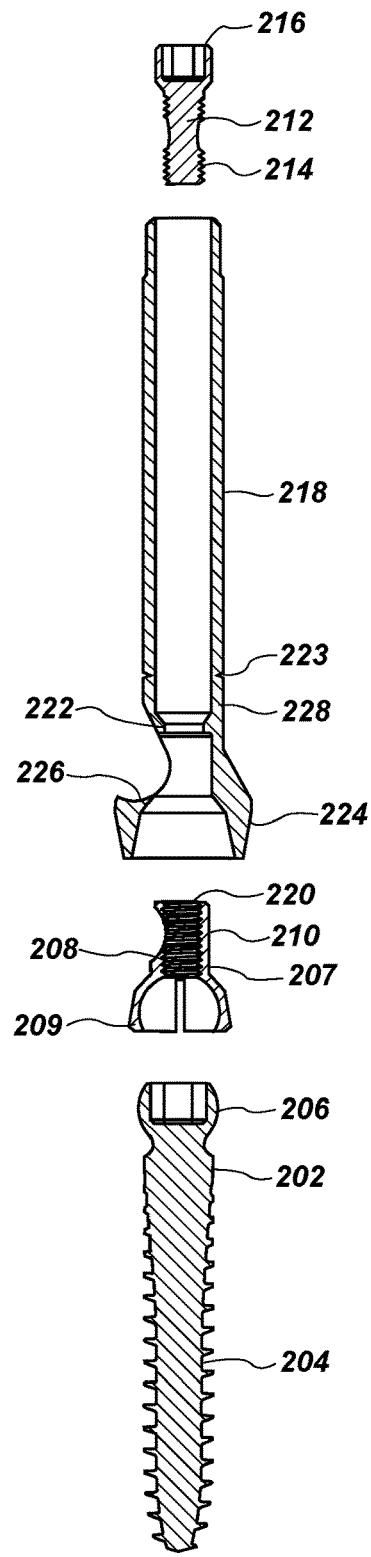
FIG. 16 is an exploded cross-sectional view of the embodiment of FIG. 15.

The spine alignment system 200 also includes a spindle 212 that includes a threaded distal end 214 and a proximal head 216. As shown in FIG. 16, the collet 207 includes an interior threaded surface 220 within the cylindrical portion 210. The interior threaded surface 220 is configured to threadedly engage with the threaded distal end 214 of the spindle 212.

During use and assembly, the pedicle screw 202 can be inserted and secured to the bony pedicle of a desired vertebrae. Then the collet 207 can be placed over the head 206 of the pedicle screw 202. The collet 207 can then be inserted into the distal end of the extension shaft 218. The spindle 212 can then be inserted into the proximal end of the extension shaft 118 until the spindle 212 is threadedly engaged with the collet 207.

Figure 17:
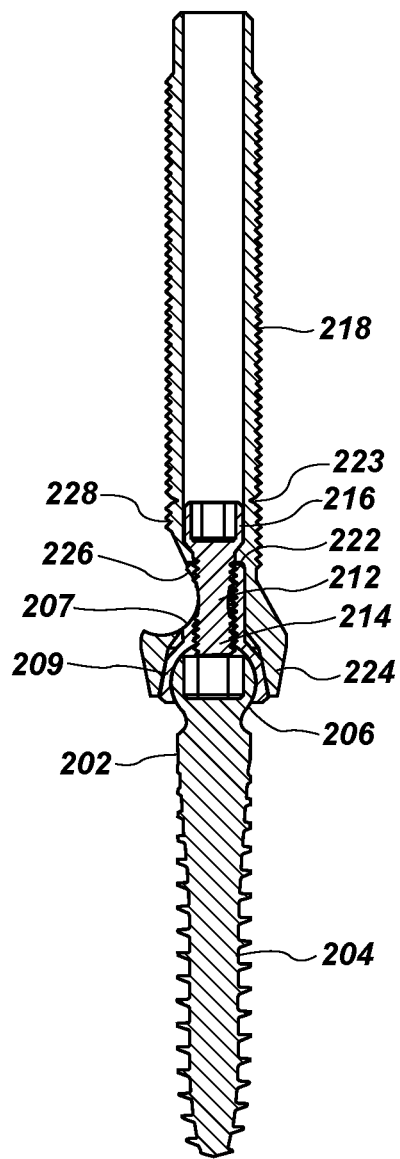
FIG. 17 is an assembled cross-sectional view of the embodiment of FIG. 15.
Figure 18:
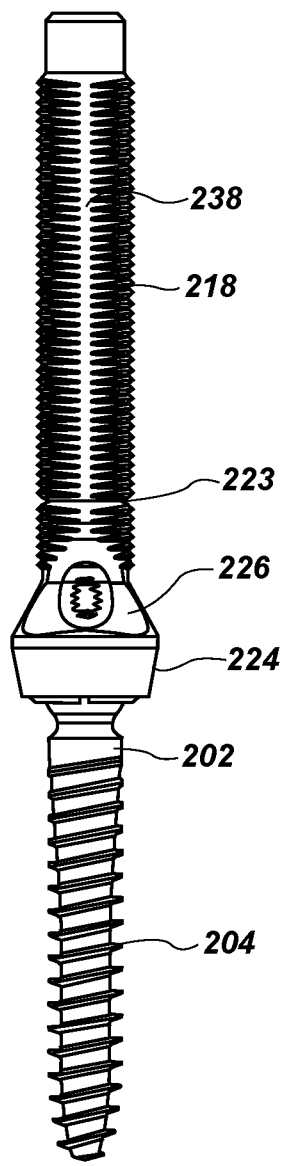
FIG. 18 is an assembled front view of the embodiment of FIG. 15.
Figure 21:
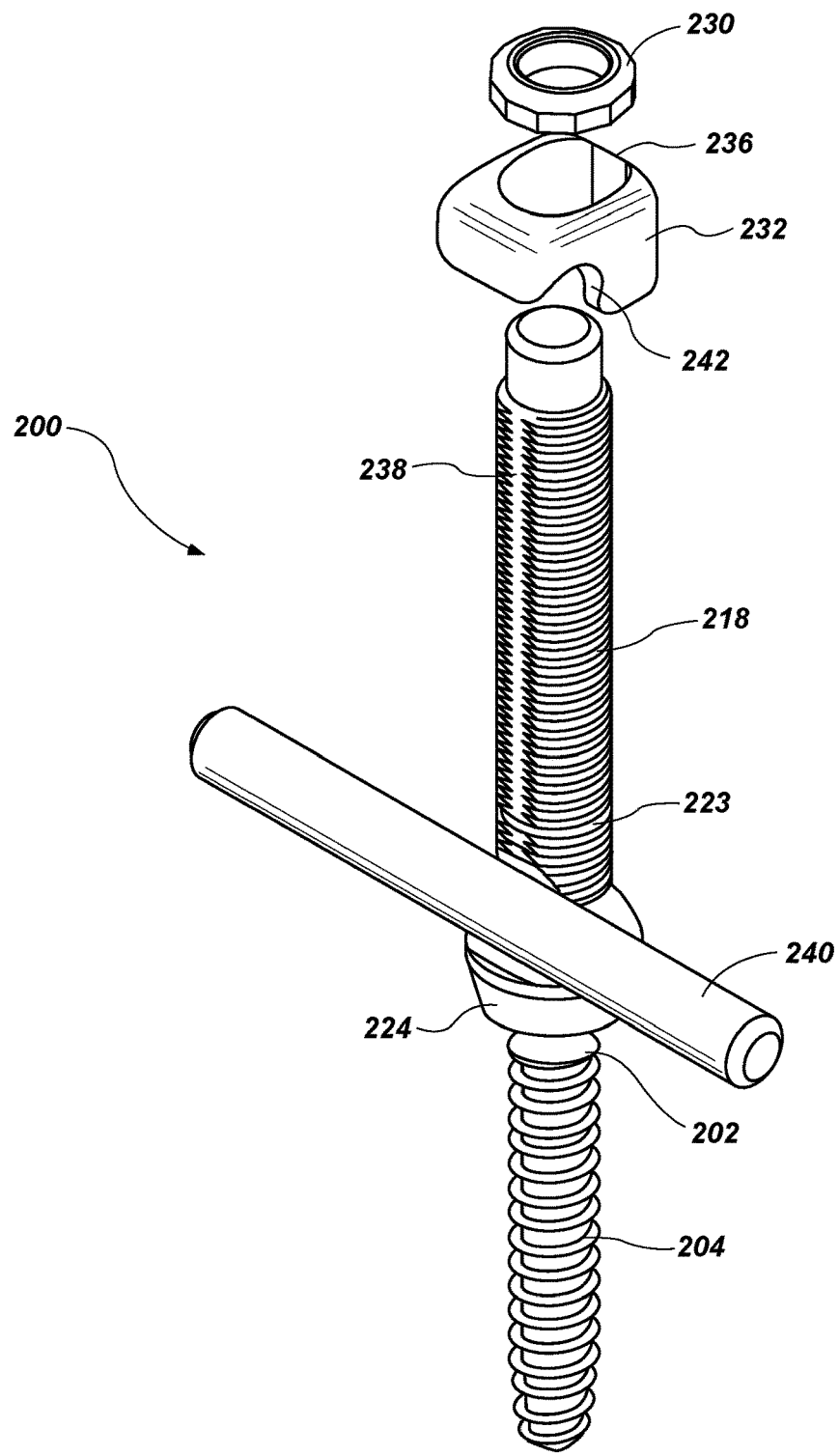
FIG. 21 is an exploded perspective view of the embodiment of FIG. 15, including a cap and an alignment rod.
Figure 22:
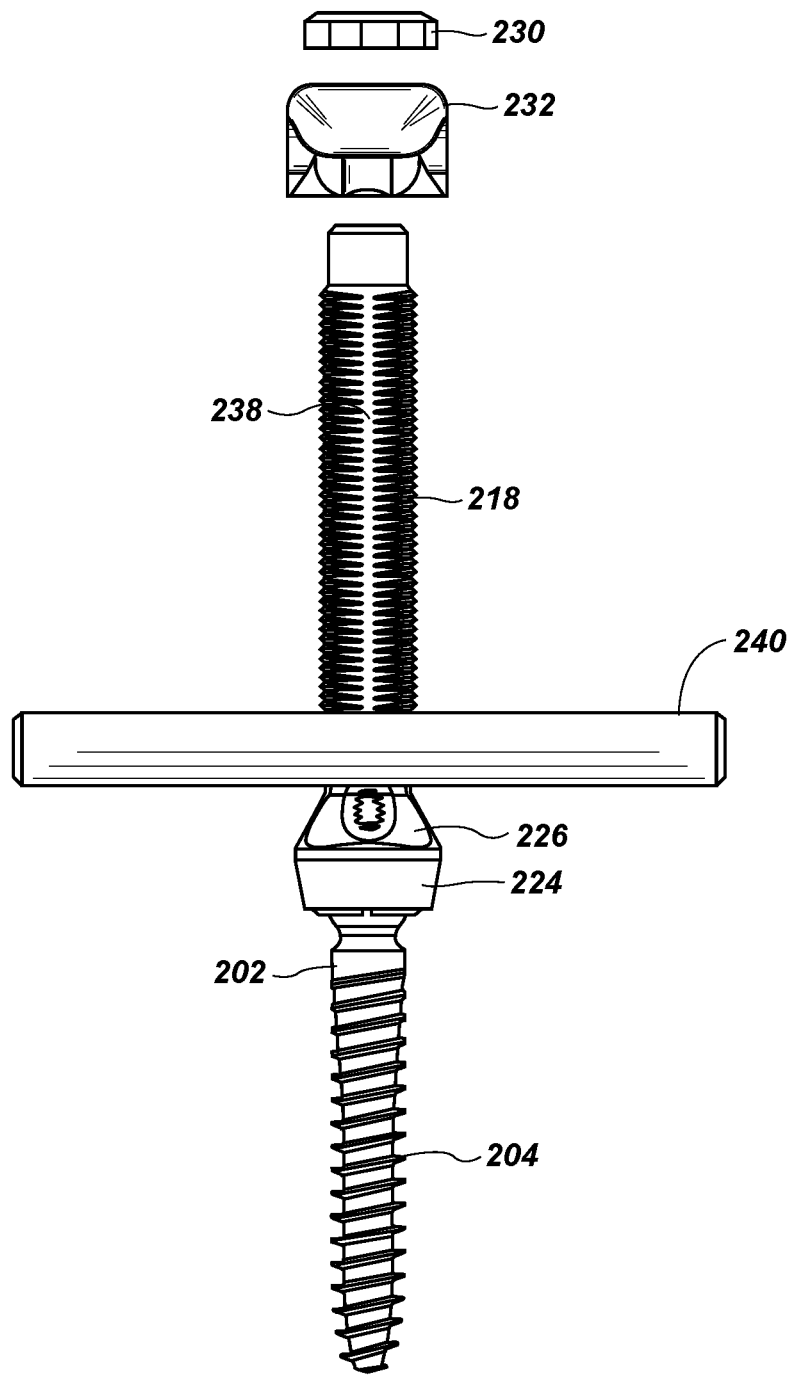
FIG. 22 is an exploded front view of the embodiment of FIG. 21 and as illustrated in FIG. 21.
Figure 23:
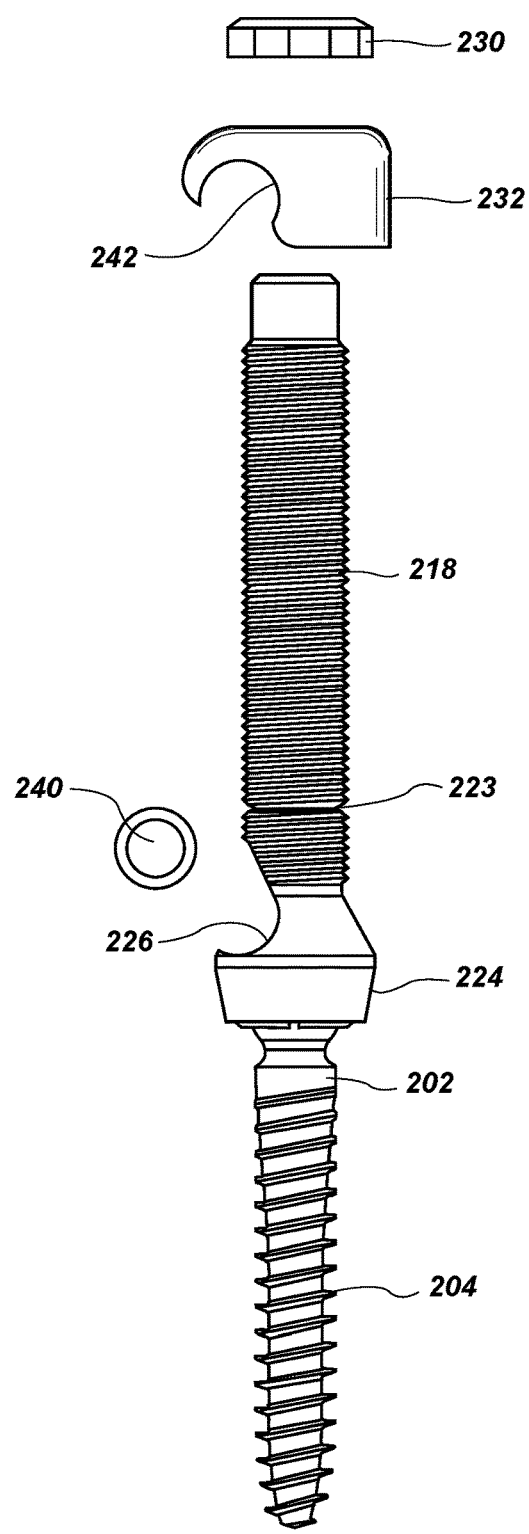
FIG. 23 is an exploded side view of the embodiment of FIG. 21.
Figure 24:
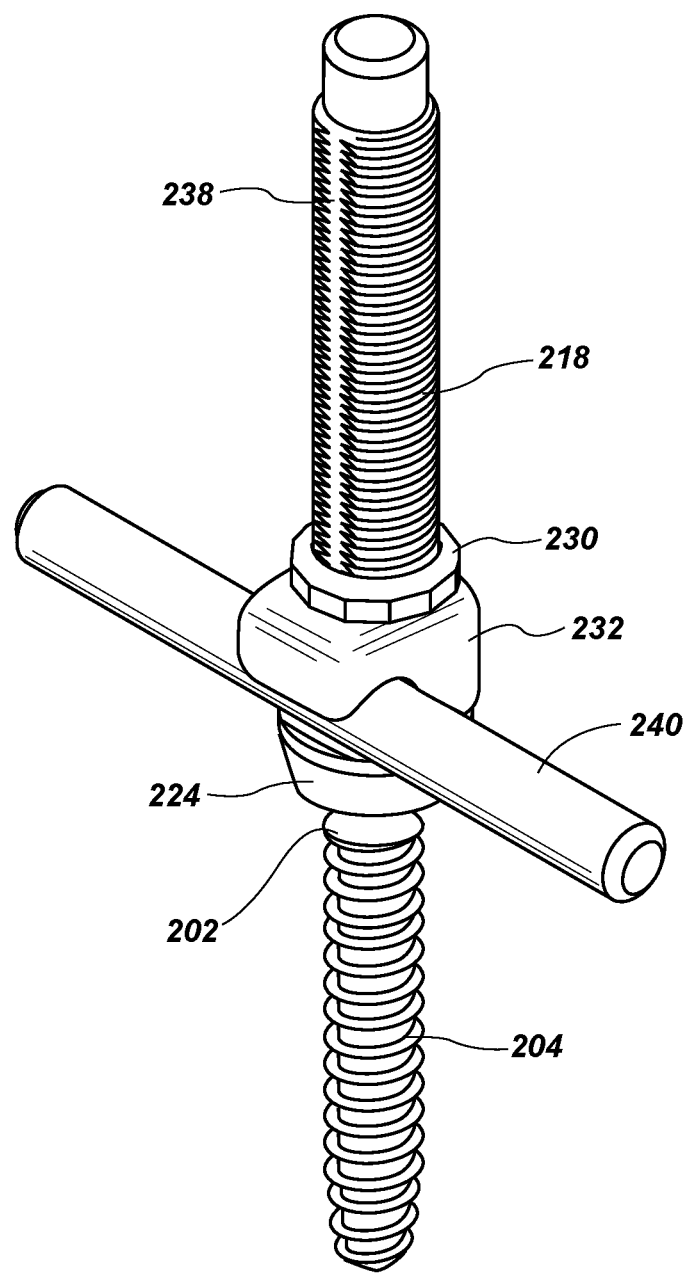
FIG. 24 is an assembled, perspective view of the embodiment of FIG. 21.
Figure 25:
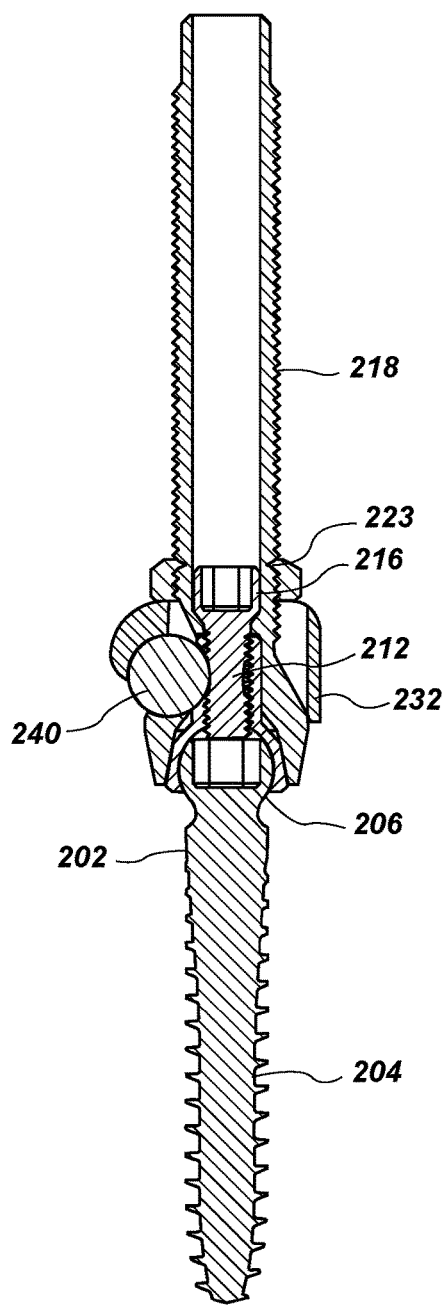
FIG. 25 is an assembled cross-sectional view of the embodiment of FIG. 21.

As shown in FIG. 17, the spindle 212 can rest against an interior flange 222 of the extension shaft 218 such that as the spindle 212 drives into the collet 207, the collet 207 is pulled further and further into the extension shaft 218 until the cylindrical portion 210 of the collet 207 abuts the interior flange 222, opposite to the spindle 212. The head 216 of the spindle 212 is configured to receive and be driven by a power or manual driver.

As the collet 207 is pulled into the extension shaft 218, the receiving bore 209 is tightened by contact with the distal end of the extension shaft 218. As the receiving bore 209 is tightened, the receiving bore 209 is rigidly secured to the head 206 of the pedicle screw 202, such that the pedicle screw will not be able to translate or rotate with respect to the collet 207.

The extension shaft 218 also includes a head 224 having a generally conical shape. The head 206 includes an approximately C-shaped cut-out portion 226, or slot, located substantially on a side of the head 224. The slot 226 includes a longitudinal axis that is substantially perpendicular to the longitudinal axis of the pedicle screw 202. The slot 226 is substantially coaxial with slot 208 of the collet 207 when fully assembled. The conical shape of the head 224 transitions to a cylindrical shape above the slot 226, resulting in a cylindrical portion 228. The cylindrical portion 228 includes an exterior thread configured to receive a locking nut 230.

The extension shaft 218 includes external threads that are formed to match the threads on the cylindrical portion 228 of the head 224 such that the locking nut 230 can threadedly engage the extension shaft 218 and the cylindrical portion 228 of the head 224.

The extension shaft 118 can be integrated with the head 224 with a fracture groove cut 223 between the extension shaft 218 and the head 224, which can enable the extension shaft 218 to break-away from the head 224 after installation of the spine alignment system 200.

As shown in FIGS. 21-25, the extension shaft 218 is configured to receive a cap 232. The cap 232 includes an approximately shaped oblong through hole 234, substantially similar as that provided in cap 132 discussed above, which includes a substantially flat side surface 236 that is configured to lie flat against a flat side surface 238 of the extension shaft 218. The extension shaft 218 includes a pair of opposing flat side surfaces 238, one of the pair of flat surfaces 238 faces the same direction as the slot 226 of the head 224. These flat side surfaces 238 serve as a guide for the cap 232 after capturing an alignment rod 240 and translating down the length of the extension shaft 218. The alignment rod 240 is captured by the cap 232 within an approximately C-shaped cutout 242, or slot, which is formed and dimensioned to substantially the same diameter as the alignment rod 240 so as to securely capture the alignment rod 240.

One of the pair of flat surfaces 238 engages the alignment rod 240, helping secure the alignment rod 240 in place during axial translation of the cap 232 and the opposing flat surface 238 can engage the flat surface 236 within the cap 232, helping to prevent unwanted rotation of the cap 232 during axial translation down the extension shaft 218.

During assembly or use, a surgeon or user can place the cap 232 onto the proximal portion of the extension shaft 218. After the cap 232 is engaged to the extension shaft 218, the surgeon can then capture the alignment rod 240 with the slot 242 of the cap 232. The cap 232 can then carry the alignment rod 240 down the length of the extension shaft 218 until the alignment rod 240 is captured and secured between the slot 242 of the cap 232 and the slot 226 of the head 224.

Figure 26:
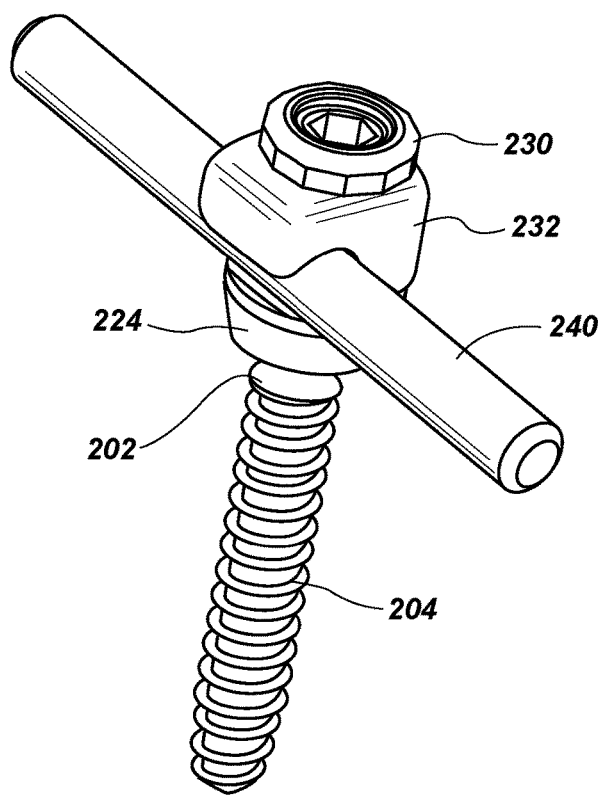
FIG. 26 is an assembled perspective view of the embodiment of FIG. 21 without an extension shaft.

The cap 232 can be pushed down the length of the extension shaft 218 by the locking nut 230. The locking nut 230 is threadedly engaged with the extension shaft 218 above the cap 232, such that as the surgeon drives the locking nut 230, the locking nut 230 pushes the cap 232 toward the head 224. The surgeon can then drive the locking screw until the cap 232 secures the alignment rod 240 to the head 224. Once fulled secured, the slot 242 of the cap 232 and the slot 226 of the head 224 will surround the circumference of the alignment rod 240, although not fully, enough to prevent the alignment rod 240 from breaking away from the pedicle screw 202 in a lateral direction. The cylindrical portion 228 of the head 224 has sufficient length to accommodate both the cap 232 and the locking nut 230 when fully secured, such that, the extension shaft 218 can then be removed or broken from engagement with the head 224, as shown in FIG. 26.

In accordance with a beneficial methods in accordance with the present disclosure, multiple spine alignment systems 200 can be secured to corresponding vertebra that a surgeon is attempting to set in alignment. Once all of the desired pedicle screws 202 are secured to the corresponding vertebra and corresponding extension shafts 218 are secured to the pedicle screws 202, caps 232 capturing the alignment rod 240 can be incrementally translated down their corresponding extension shafts 218 until the alignment rod 240 is secured to each of the heads 224 and pedicle screws 202. This incremental translation of the caps 232 and alignment rod 240 can provide load sharing across the entire series of pedicle screws 202, decreasing the stress at individual bone-screw interfaces. Additionally, the incremental securement of the alignment rod 240 to the pedicle screws 202 can serve as a reduction tool, bringing all of the desired vertebrae into alignment with the alignment rod 240, thereby reducing the number of tools, steps and duration of a surgical procedure.

Another exemplary advantage of the spine alignment system 200 is that a surgeon can drive the pedicle screw 202, spindle 212, and the locking nut 230 with a power driven instrument, thus removing the need for manual and often laborious tightening and alignment of the alignment rod 240 to the corresponding pedicle screws 202.

Figure 27:
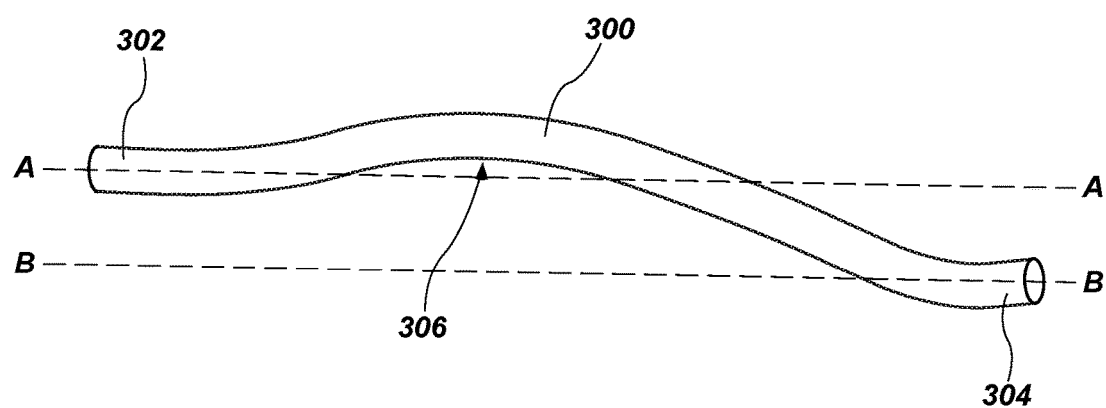
FIG. 27 is an embodiment of a contoured alignment rod.

In an alternative embodiment, as shown in FIG. 27, an alignment rod 300 can be contoured. The alignment rod 300 is not linear, having a first end 302 and a second end 304, where the first end 302 and the second end 304 are not co-linear. Instead, the alignment rod 300 is contoured, having at least one curvature 306. In alternative embodiments the alignment rod 306 may include any desired number of curvatures, having varying or identical dimensions.

Additionally, a longitudinal axis A of the first end 302 is not coaxial with the longitudinal axis B of the second end 304. However, the longitudinal axis A may be substantially parallel to the Longitudinal axis B, as shown in FIG. 27, or the longitudinal axis A may intersect with the longitudinal axis B.

The curvature 306 can be of custom size and dimension depending on the specific needs of the patient. For example, a surgeon can decide that the alignment of a spine should occur in multiple stages, thus utilizing the contoured alignment rod 300 can be a beneficial intermediate step toward straightening the alignment of a spine.

Each of the components of the spine alignment systems 100 and 200 can be fabricated from titanium or a titanium alloy, cobalt chrome, or stainless steel or other materials known to those skilled in the art.

FIGS. 28-33, illustrate how multiple spine alignment systems 100 can be secured to corresponding vertebra 402 of a spine 400 that a surgeon is attempting to align. Systems 100 are identified by references numerals in only a representative number, however, it can be assumed that the systems or other corresponding elements that are not specifically identified by a reference numeral, are identical or substantially similar to the corresponding enumerated elements.

Figure 29:
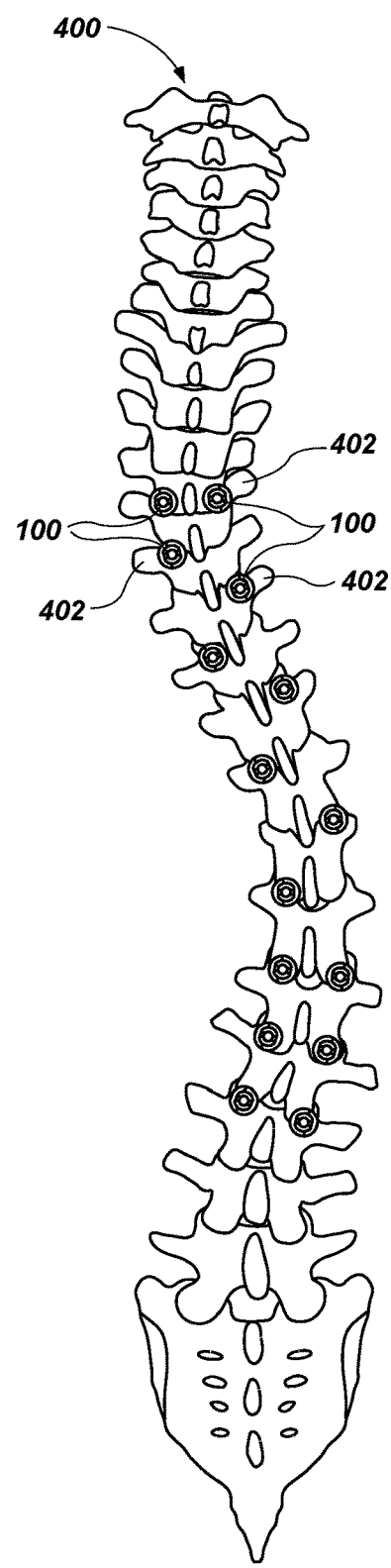
FIG. 29 is top view of the embodiment of FIG. 28 before alignment rods are secured.
Figure 31:
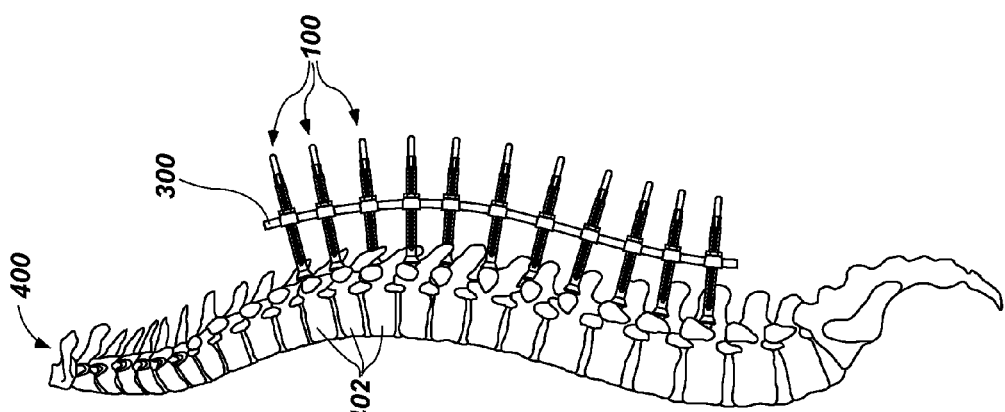
FIG. 31 is a partially assembled view of the embodiment of FIG. 28.
Figure 30:
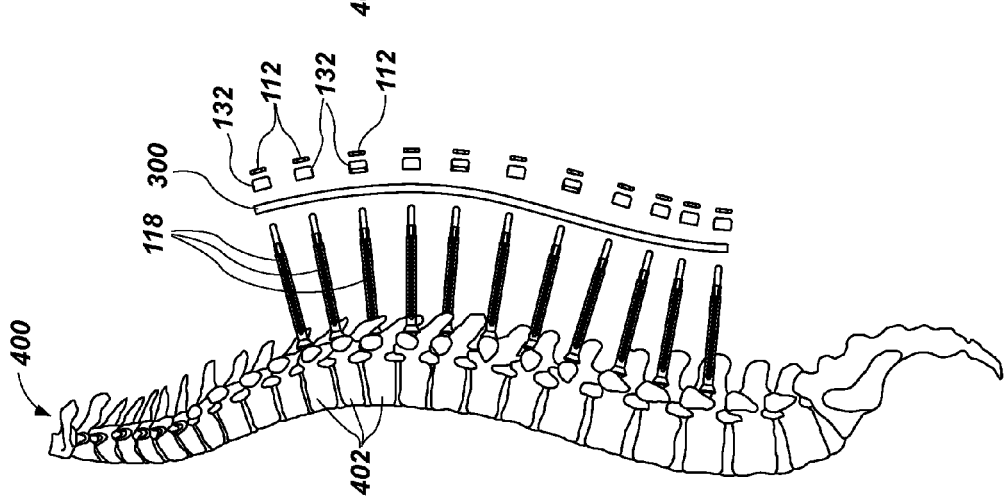
FIG. 30 is an exploded view of the embodiment of FIG. 28.

As shown in FIG. 29, each of the pedicle screws 102 are first secured to corresponding vertebra 402. As shown in FIG. 30-31, caps 132 can be used to capture and secure the alignment rod 140. As the alignment rod 300 is aligned and brought into contact with the extension shafts 118 of the systems 100, the caps 132 can be incrementally translated down their corresponding extension shafts 118 until the alignment rod 300 is secured to each of the heads 106 of the pedicle screws 102.

A surgeon or user can insert and secure the pedicle screws 102 (included in system 100), with the adjoined extension shaft 118, to the bony pedicle of a desired vertebra 402. Once the pedicle screw 102 is secured, the surgeon can then place the cap 132 onto the proximal portion of the extension shaft 118.

After the cap 132 is engaged to the extension shaft 118, the surgeon or user can then capture the alignment rod 140 with the slot 142 of the cap 132, as discussed in more detail previously. The cap 132 can then carry the alignment rod 300 down the length of the extension shaft 118 until the alignment rod 300 is captured and secured between the slot 142 of the cap 132 and the slot 108 of the head 106 of the pedicle screw 102, as discussed above.

The series of caps 132, included in systems 100 in FIGS. 28-33, are incrementally translated down the length of the extension shafts 118 by corresponding locking nuts 112. The locking nuts 112 are threadedly engaged with the extension shafts 118 above the caps 132, such that as the surgeon drives the locking nuts 112, the locking nuts 112 push the cap 132 toward the head 106 of the pedicle screw 102. The surgeon can then drive the locking nuts 112 until the caps 132 secure the alignment rod 300 to the heads 106 of the pedicle screws 102.

Figure 33:
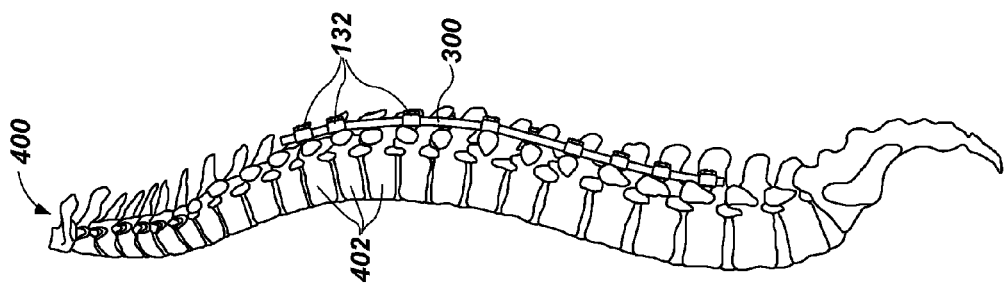
Figure 32:
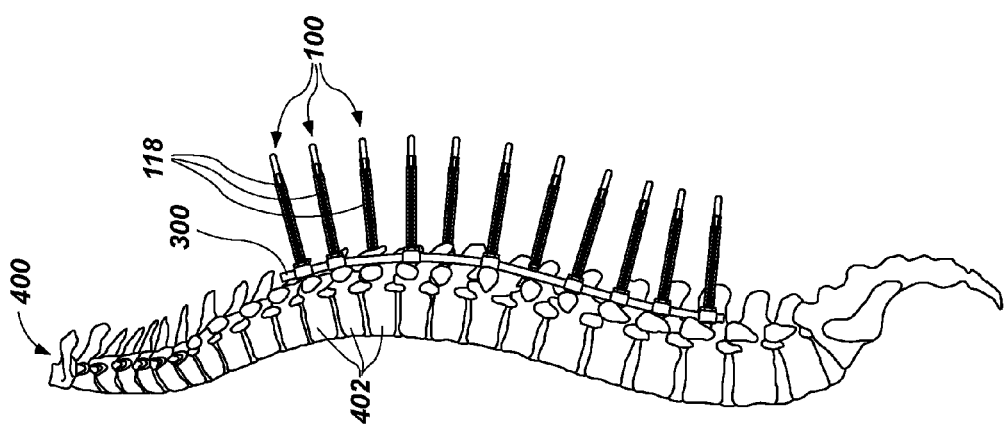
FIG. 32 is a further assembled view of view of the embodiment of FIG. 28; and, FIG. 33 is side view of a fully assembled embodiment of FIG. 28.

As shown in FIG. 33, once the alignment rods 300 are fully secured, the extension shafts 118 can then be removed from engagement with the pedicle screw 102, as discussed in more detail above.

Figure 28:
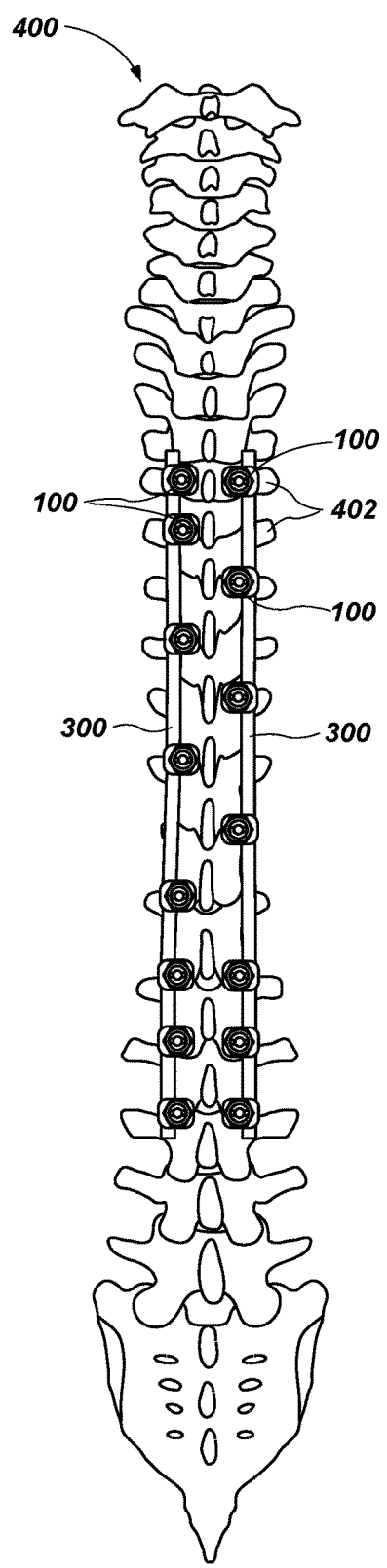
FIG. 28 is top view of an embodiment of the disclosed spine alignment system.

The incremental translation of the caps 132 and alignment rods 300 can provide load sharing across the entire series of pedicle screws 102, decreasing the stress at individual bone-screw interfaces. Additionally, the incremental securement of the alignment rod 140 to the corresponding pedicle screws 102 can serve as a reduction tool, as shown in FIG. 28, bringing all of the desired vertebrae into alignment with the alignment rod 300, thereby reducing the number of tools and steps during a surgical procedure. As also shown in FIG. 28, two alignment rods 300 can be used, substantially parallel to one another and also parallel with the aligned spine 400, to provide sufficient support for the aligned spine 400 and reduce the stress on any specific vertebra 402 or side of the vertebra 402.

Another advantage of the spine alignment system is that a surgeon can drive the pedicle screw 102 and the locking nut 112 with a powered driving instrument, thus removing the need for manual and often laborious tightening and alignment of the alignment rod 140 to the corresponding pedicle screws 102. It will be appreciated that the use of a such a driver, whatever the source of the power, can greatly improve the efficiency of the surgical procedure and thus beneficially reduce the time required to complete the procedure.

And yet another advantage of the disclosed spine alignment system occurs during use with patients that have a substantial amount of fat around the area of the spine 400. Conventionally, when dealing with such patients it can be very difficult for a surgeon to access and manipulate the components of a convention spine alignment system because of the depth of the spine with respect to the exterior of the patient's back, requiring a deeper access cavity to be cut into the patient's back. The disclosed spine alignment system, however, provides that the extension shafts 118 extend well above the spine 400 allowing the surgeon to readily manipulate the vertebrae 402 and the alignment rod 300 in such patients which increases the ease and efficiency which a surgeon can secure the spine alignment system in place with respect to the spine 400.

It is to be understood that the above-described arrangements are only illustrative of the application of the principles of the present disclosure. Numerous modifications and alternative arrangements may be devised by those skilled in the art without departing from the spirit and scope of the present disclosure are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A spine alignment system, comprising:
a pedicle screw having a longitudinal axis, the pedicle screw having a screw head, wherein the screw head includes a slot having a longitudinal axis that is substantially perpendicular to the longitudinal axis of the pedicle screw, and a key slot also extending substantially perpendicular to the longitudinal axis of the pedicle screw;
an extension shaft secured to the pedicle screw, such that a longitudinal axis of the extension shaft is substantially coaxial with the longitudinal axis of the pedicle screw, wherein the extension shaft includes a key that is received within the key slot of the screw head, and the wherein the extension shaft is generally cylindrical in shape and includes at least one substantially flat exterior surface parallel with the longitudinal axis of the extension shaft;
a cap having a through-hole configured to receive the extension shaft, the through-hole having a longitudinal axis, wherein the cap includes a slot having a longitudinal axis that is substantially perpendicular to the longitudinal axis of the through-hole, and wherein the slot of the screw head and the slot of the cap, together, form a substantially cylindrical passage configured to receive an alignment rod; and,
a nut configured to receive the extension shaft and facilitate movement of the cap along the extension shaft.

2. The system of claim 1, wherein the pedicle screw is mono-axial.

3. The system of claim 1, wherein the head of the pedicle screw includes an exterior thread that threadedly engages the nut, wherein the nut secures the cap to the head of the pedicle screw.

4. The system of claim 1, further comprising:
an alignment rod, wherein the alignment rod is received by the substantially cylindrical passage formed by the pedicle screw head and the cap, such that the alignment rod is laterally fixed within the substantially cylindrical passage.

5. The system of claim 4, wherein the alignment rod is substantially linear.

6. The system of claim 4, wherein the alignment rod is curved along a longitudinal axis.

7. The system of claim 4, wherein the slot of the cap is configured to retain the alignment rod in a snap-fit engagement.

8. The system of claim 1, wherein the cap includes a substantially planar surface within the through-hole.

9. The system of claim 8, wherein the substantially planar surface of the cap is located on an opposite side of the through-hole from the slot of the cap.

10. The system of claim 1, wherein the slot of the cap extends more than 180 degrees in circumference.

11. A spine alignment system, comprising:
a pedicle screw having a longitudinal axis, the pedicle screw having a screw head, wherein the screw head includes a slot having a longitudinal axis that is substantially perpendicular to the longitudinal axis of the pedicle screw, and a key slot also extending substantially perpendicular to the longitudinal axis of the pedicle screw;
an extension shaft secured to the pedicle screw, such that a longitudinal axis of the extension shaft is substantially coaxial with the longitudinal axis of the pedicle screw, wherein the extension shaft also includes a head, wherein the head includes a slot having a longitudinal axis that is substantially perpendicular to the longitudinal axis of the pedicle screw, wherein the extension shaft includes a key that is received within the key slot of the screw head, and wherein the extension shaft is generally cylindrical in shape and includes at least one substantially flat exterior surface parallel with the longitudinal axis of the extension shaft;

a cap having a through-hole configured to receive the extension shaft, the through-hole having a longitudinal axis, wherein the cap includes a slot having a longitudinal axis that is substantially perpendicular to the longitudinal axis of the through-hole, and wherein the slot of the head and the slot of the cap, together, form a substantially cylindrical passage configured to receive an alignment rod; and, a nut configured to receive the extension shaft and facilitate movement of the cap along the extension shaft.

12. The system of claim 11, wherein the head of the extension shaft includes a exterior thread that threadedly engages the nut, wherein the nut secures the cap to the head of the pedicle screw.

13. The system of claim 11, wherein the pedicle screw is poly-axial.

14. The system of claim 11, further comprising:
an alignment rod, wherein the alignment rod is received by the substantially cylindrical passage formed by the pedicle screw head and the cap, such that the alignment rod is laterally fixed within the substantially cylindrical passage.

15. The system of claim 14, wherein the alignment rod is substantially linear.

16. The system of claim 14, wherein the alignment rod is curved along a longitudinal axis.

17. The system of claim 14, wherein the slot of the cap is configured to retain the alignment rod in a snap-fit engagement.

18. The system of claim 11, wherein the cap includes a substantially planar surface within the through-hole.

19. The system of claim 18, wherein the substantially planar surface of the cap is located on an opposite side of the through-hole from the slot of the cap.

20. The system of claim 11, wherein the slot of the cap extends more than 180 degrees in circumference.

21. A method of assembling a spine alignment system, comprising:
securing a pedicle screw, having a head, to a bony pedicle of a vertebra, wherein the pedicle screw includes a key slot extending substantially perpendicular to a longitudinal axis of the pedicle screw;
securing an extension shaft to a pedicle screw, wherein the extension shaft includes a key that is received within the key slot of the screw head, and wherein the extension shaft is generally cylindrical in shape and includes at least one substantially flat exterior surface parallel with the longitudinal axis of the extension shaft;
engaging a cap about the extension shaft such that the cap can translate axially over a length of the extension shaft, the cap having a slot having a longitudinal axis that is substantially perpendicular to a longitudinal axis of the extension shaft when the cap is engaged with the extension shaft;
capturing an alignment rod with the slot of the cap;
incrementally translating the cap and alignment rod axially down the extension shaft; and,
securing the alignment rod to the pedicle screw such that the alignment rod cannot be moved laterally with respect to the pedicle screw.

22. The method of claim 21, further comprising:
aligning a plurality of vertebra along the alignment rod as the alignment rod is incrementally translated down the extension shaft.

23. The method of claim 21, wherein the head of the pedicle screw includes an exterior thread that threadedly engages a nut, wherein the nut secures the cap to the head of the pedicle screw.

24. The method of claim 21, wherein the pedicle screw is poly-axial.

25. The method of claim 21, wherein the alignment rod is substantially linear.

26. The method of claim 21, wherein the alignment rod is curved along a longitudinal axis.

27. The method of claim 21, wherein the pedicle screw is mono-axial.

28. A method of assembling a spine alignment system, comprising:
securing a pedicle screw, having a head, to a bony pedicle of a vertebra, wherein the pedicle screw includes a key slot extending substantially perpendicular to a longitudinal axis of the pedicle screw;
securing an extension shaft to a pedicle screw, wherein the extension shaft includes a key that is received within the key slot of the screw head, and wherein the extension shaft is generally cylindrical in shape and includes at least one substantially flat exterior surface parallel with the longitudinal axis of the extension shaft;
engaging an alignment rod with the extension shaft such that the alignment rod can translate over a length of the extension shaft,
incrementally translating alignment rod axially down the extension shaft; and,
securing the alignment rod to the pedicle screw such that the alignment rod cannot be moved laterally with respect to the pedicle screw.

29. The method of claim 28, further comprising:
engaging a cap about the extension shaft such that the cap can translate axially over a length of the extension shaft, the cap having a slot having a longitudinal axis that is substantially perpendicular to a longitudinal axis of the extension shaft when the cap is engaged with the extension shaft; and
capturing the alignment rod with the slot of the cap.

30. The method of claim 29, further comprising:
incrementally translating the cap and the alignment rod axially down the extension shaft.

31. The method of claim 29, wherein the head of the pedicle screw includes an exterior thread that threadedly engages a nut, wherein the nut secures the cap to the head of the pedicle screw.

32. The method of claim 28, further comprising:
aligning a plurality of vertebra along the alignment rod as the alignment rod is incrementally translated down the extension shaft.

33. The method of claim 28, wherein securing of the pedicle screw and extension shaft is performed by a power driving instrument.

34. A spine alignment system, comprising:
a pedicle screw having a longitudinal axis, the pedicle screw having a screw head, wherein the screw head includes a slot having a longitudinal axis that is substantially perpendicular to the longitudinal axis of the pedicle screw, and the pedicle screw includes a key slot extending substantially perpendicular to a longitudinal axis of the pedicle screw;

an extension shaft secured to the pedicle screw, such that a longitudinal axis of the extension shaft is substantially coaxial with the longitudinal axis of the pedicle screw, wherein the extension shaft is detachable from the pedicle screw, and the extension shaft includes a key that is received within the key slot of the screw head, and wherein the extension shaft is generally cylindrical in shape and includes at least one substantially flat exterior surface parallel with the longitudinal axis of the extension shaft; and an alignment rod configured to engage with the extension shaft such that the alignment rod is configured to translate axially along the extension shaft.

35. The system of claim 34, further comprising:

a cap having a through-hole configured to receive the extension shaft, the through-hole having a longitudinal axis, wherein the cap includes a slot having a longitudinal axis that is substantially perpendicular to the longitudinal axis of the through-hole, and wherein the slot of the screw head and the slot of the cap, together, form a substantially cylindrical passage configured to receive the alignment rod.

36. The system of claim 35, further comprising:

a nut configured to receive the extension shaft and facilitate movement of the cap along the extension shaft.

37. The system of claim 35, wherein the alignment rod is received by the substantially cylindrical passage formed by the pedicle screw head and the cap, such that the alignment rod is laterally fixed within the substantially cylindrical passage.

38. The system of claim 34, wherein the extension shaft is configured to receive a power driving instrument, to facilitate the powered driving of the extension shaft and the pedicle screw.

* * * * *